US011420941B2

(12) United States Patent
Kuimelis et al.

(10) Patent No.: US 11,420,941 B2
(45) Date of Patent: Aug. 23, 2022

(54) METHODS AND SYSTEMS FOR MASK ALIGNMENT IN MANUFACTURING PROCESS OF ARRAYS

(71) Applicant: Cowper Sciences Inc., Chandler, AZ (US)

(72) Inventors: Robert Kuimelis, Palo Alto, CA (US); Gaurav Saini, Chandler, AZ (US); David Smith, Scottsdale, AZ (US); Tommy Armsby, Tempe, AZ (US)

(73) Assignee: COWPER SCIENCES INC., Chandler, AZ (US)

( * ) Notice: Subject to any disclaimer, the term of this patent is extended or adjusted under 35 U.S.C. 154(b) by 905 days.

(21) Appl. No.: 16/024,171

(22) Filed: Jun. 29, 2018

(65) Prior Publication Data

US 2019/0002410 A1 Jan. 3, 2019

Related U.S. Application Data

(60) Provisional application No. 62/526,660, filed on Jun. 29, 2017.

(51) Int. Cl.
| | |
|---|---|
| *G03F 7/20* | (2006.01) |
| *C07D 233/02* | (2006.01) |
| *C07C 233/13* | (2006.01) |
| *C07F 7/18* | (2006.01) |
| *G03F 9/00* | (2006.01) |
| *C07C 319/06* | (2006.01) |
| *C07C 231/12* | (2006.01) |

(52) U.S. Cl.
CPC .......... *C07D 233/02* (2013.01); *C07C 231/12* (2013.01); *C07C 233/13* (2013.01); *C07C 319/06* (2013.01); *C07F 7/18* (2013.01); *G03F 7/70616* (2013.01); *G03F 7/70633* (2013.01); *G03F 9/7088* (2013.01)

(58) Field of Classification Search
None
See application file for complete search history.

(56) References Cited

U.S. PATENT DOCUMENTS

| | | | | |
|---|---|---|---|---|
| 5,143,854 | A | * 9/1992 | Pirrung | G01N 21/6428 436/518 |
| 5,384,261 | A | 1/1995 | Winkler et al. | |
| 5,424,186 | A | 6/1995 | Fodor et al. | |
| 5,565,332 | A | 10/1996 | Hoogenboom et al. | |
| 5,571,639 | A | 11/1996 | Hubbell et al. | |
| 6,083,697 | A | 7/2000 | Beecher et al. | |
| 6,153,743 | A | 11/2000 | Hubbell et al. | |
| 2002/0068157 | A1 | * 6/2002 | Wischerhoff | G01N 33/54353 428/212 |
| 2003/0050438 | A1 | 3/2003 | Montgomery | |
| 2004/0038556 | A1 | 2/2004 | French et al. | |
| 2004/0063902 | A1 | 4/2004 | Miranda | |
| 2004/0110212 | A1 | * 6/2004 | McCormick | B01J 19/0046 435/6.11 |
| 2005/0156499 | A1 | 7/2005 | Dinu et al. | |
| 2005/0214803 | A1 | * 9/2005 | Wang | G01N 33/54353 435/6.12 |
| 2007/0122841 | A1 | 5/2007 | Rajasekaran et al. | |
| 2007/0122842 | A1 | 5/2007 | Rajasekaran et al. | |
| 2008/0124719 | A1 | 5/2008 | Chung et al. | |
| 2009/0258796 | A1 | 10/2009 | Rajasekaran et al. | |
| 2010/0261205 | A1 | 10/2010 | Kakuta et al. | |
| 2011/0105366 | A1 | 5/2011 | Lebl et al. | |
| 2015/0141296 | A1 | 5/2015 | Woodbury et al. | |
| 2015/0217258 | A1 | 8/2015 | Woodbury et al. | |

FOREIGN PATENT DOCUMENTS

| | | |
|---|---|---|
| WO | WO-9727329 A1 | 7/1997 |
| WO | WO-2008151146 A2 | 12/2008 |
| WO | WO-2013063133 A1 | 5/2013 |
| WO | WO-2014062981 A1 | 4/2014 |

OTHER PUBLICATIONS

Boltz, et al. Peptide microarrays for carbohydrate recognition. Analyst. Apr. 2009;134(4):650-2. doi: 10.1039/b823156g. Epub Feb. 11, 2009.
Fodor et al., Light-directed, spatially addressable parallel chemical synthesis, Science, Feb. 1991, 767-73, vol. 251, No. 4995.
Fu et al., Exploring peptide space for enzyme modulators, J. Am. Chem. Soc., Apr. 2010, 6419-6424, vol. 132, No. 18.
Fu et al., Interenzyme substrate diffusion for an enzyme cascade organized on spatially addressable DNA nanostructures, J Am Chem Soc., Mar. 2012, 5516-9, vol. 134, No. 12.
Fu, et al. Peptide-modified surfaces for enzyme immobilization. PLoS One. Apr. 8, 2011;6(4):e18692. doi: 10.1371/journal.pone.0018692.
Greving et al., Feature-level MALDI-MS characterization of in situ-synthesized peptide microarrays, Langmuir, Feb. 2009, 1456-1459, vol. 26, No. 3.
Gupta, N., et al. Engineering a synthetic ligand for tumor necrosis factor-alpha.(2011) Bioconjugate Chemistry, vol. 22, pp. 1473-1478.
Han et al., DNA origami with complex curvatures in three-dimensional space, Science, Apr. 2011, 342-346, vol. 332, No. 6027.
Hughes, et al. Immunosignaturing can detect products from molecular markers in brain cancer. PLoS One. 2012;7(7):e40201. doi: 10.1371/journal.pone.0040201. Epub Jul. 16, 2012.
International search report and written opinion dated Oct. 22, 2012 for PCT/US2012/036631.
International search report dated Dec. 20, 2013 for PCT/US2013/065541.
Ke et al., Self-assembled water-soluble nucleic acid probe tiles for label-free RNA hybridization assays, Science, Jan. 2008, 180-183, vol. 319, No. 5860.

(Continued)

*Primary Examiner* — Christopher M Gross
(74) *Attorney, Agent, or Firm* — Wilson Sonsini Goodrich & Rosati

(57) ABSTRACT

Provided herein are molecules and salts thereof, arrays containing molecules and salts thereof, solid supports containing molecules and salts thereof, kits containing molecules or salts thereof, and methods of determining alignment of photolithographic masks comprising molecules or salts thereof.

15 Claims, 9 Drawing Sheets

(56) References Cited

OTHER PUBLICATIONS

Legutki, et al. A general method for characterization of humoral immunity induced by a vaccine or infection. Vaccine. Jun. 17, 2010;28(28):4529-37. doi: 10.1016/j.vaccine.2010.04.061. Epub May 5, 2010.

Lund, et al., Molecular robots guided by prescriptive landscapes, Nature, May 2010, 206-210, vol. 465, No. 7295.

Moller, et al. DNA probes on chip surfaces studied by scanning force microscopy using specific binding of colloidal gold. Nucleic Acids Res. Oct. 15, 2000;28(20):E91.

Northen et al., Combinatorial screening of biomimetic protein affinity materials, Adv Mater., Oct. 2008, 4691-4697, vol. 20, No. 24.

Price et al., On silico peptide microarrays for high-resolution mapping of antibody epitopes and diverse protein-protein interactions, Nat Med, Sep. 2012, 1434-40, vol. 18, No. 9.

Restrepo, et al. Application of immunosignatures to the assessment of Alzheimer's disease. Ann Neurol. Aug. 2011;70(2):286-95. doi: 10.1002/ana.22405.

Shan et al., Imaging local electrochemical current via surface plasmon resonance, Science, Mar. 2010, 1363-66, vol. 327, No. 5871.

Sharma et al., Control of self-assembly of DNA tubules through integration of gold nanoparticles, Science, Jan. 2009, 112-116, vol. 323, No. 5910.

Singh-Gasson et al., Maskless fabrication of light-directed oligo-nucleotide microarrays using a digital micromirror array, Nat Biotechnol, Oct. 1999, 974-978, vol. 17, No. 10.

Takulapalli et al., Electrical detection of amine ligation to a metalloporphyrin via a hybrid SOI-MOSFET, J. Am. Chem. Soc., Jan. 2008, 2226-2233, vol. 130, No. 7.

U.S. Appl. No. 13/379,080 Final Office Action Dated Jul. 21, 2015.
U.S. Appl. No. 14/116,749 Final Office Action dated May 23, 2018.
U.S. Appl. No. 14/116,749 Non-Final Office Action dated Sep. 20, 2017.
U.S. Appl. No. 14/116,749 Restriction Requirement dated Apr. 26, 2017.
U.S. Appl. No. 14/436,465 Advisory Office Action dated Dec. 4, 2017.
U.S. Appl. No. 14/436,465 Final Office Action dated Sep. 20, 2017.
U.S. Appl. No. 14/436,465 Restriction Requirement dated Dec. 6, 2017.
U.S. Appl. No. 14/436,465 Office Action dated Mar. 9, 2017.

Wilk et al., Integrated electrodes on a silicon based ion channel measurement platform, Biosensors and Bioelectronics, Sep. 2007, 183-190, vol. 23, No. 2.

Williams et al., Creating protein affinity reagents by combining peptide ligands on synthetic DNA scaffolds, J. Am Chem Soc., Dec. 2009, 17233-17241, vol. 131, No. 47.

Zhang et al., Reversible oxygen gas sensor based on electrochemiluminescence., Chemical Communications, May 2010, 3333-3335, vol. 46, No. 19.

* cited by examiner

METHODS AND SYSTEMS FOR MASK ALIGNMENT IN MANUFACTURING PROCESS OF ARRAYS

CROSS-REFERENCE

This application claims the benefit of U.S. provisional patent application No. 62/526,660 filed on Jun. 29, 2017, which is incorporated herein by reference in its entirety.

BRIEF SUMMARY

Disclosed herein are methods for determining the alignment of photolithographic masks used to print peptide features on arrays. Misalignment of lithographic masks can cause propagation of errors in printed peptide features. The disclosed methods overcome this problem by enabling verification of proper photolithographic alignment using chromophorically labelled alignment controlling regions on the array.

Disclosed herein are methods comprising (a) deprotecting a subset of a plurality of protected molecules or salts thereof comprising a photoreactive or acid-sensitive protecting group to form a plurality of deprotected molecules or salts thereof, wherein the plurality of protected molecules or salts thereof can be comprised in a first array region, and wherein the plurality of deprotected molecules or salts thereof can be comprised in a second array region; and (b) detecting alignment of the second array region with the first array region, wherein the detecting alignment can comprise detecting a chromophoric signal from at least one of the first array region and the second array region. In some aspects, the distance from a boundary of the first array region to a boundary of the second array region is substantially uniform. In some aspects, the method can be a method of monitoring an alignment of a photolithographic mask. In some aspects, the chromophoric signal can be a fluorescent signal or a phosphorescent signal. In some aspects, the first array region and the second array region can be substantially located in a space between two or more peptide features. In some aspects, the first array region and the second array region have substantially the same shape. In some aspects, the distance from the boundary of the first array region to the boundary of the second array region is non-zero. In some aspects, the deprotecting a subset of a plurality of protected molecules comprises a photolithographic mask. In some aspects, the second array region can be substantially surrounded by the first array region.

In some aspects are methods comprising: (a) deprotecting a subset of a plurality of protected molecules comprising a photoreactive or acid-sensitive protecting group to form a plurality of deprotected molecules; wherein the plurality of protected molecules are comprised in a first array region; wherein the plurality of deprotected molecules are comprised in a second array region; and (b) detecting alignment of the second array region with the first array region, wherein the detecting alignment comprises detecting a chromophoric signal from at least one of the first array region and the second array region.

In some aspects are methods comprising: (a) deprotecting a subset of a plurality of protected molecules comprising a photoreactive or acid-sensitive protecting group to form a plurality of deprotected molecules; wherein the plurality of protected molecules are comprised in a first array region; wherein the plurality of deprotected molecules are comprised in a second array region; and wherein the distance from a boundary of the first array region to a boundary of the second array region is substantially uniform; and (b) detecting alignment of the second array region with the first array region, wherein the detecting alignment comprises detecting a chromophoric signal from at least one of the first array region and the second array region.

In some aspects are methods wherein at least some of molecules of the plurality of protected molecules or salts thereof independently have the structure:

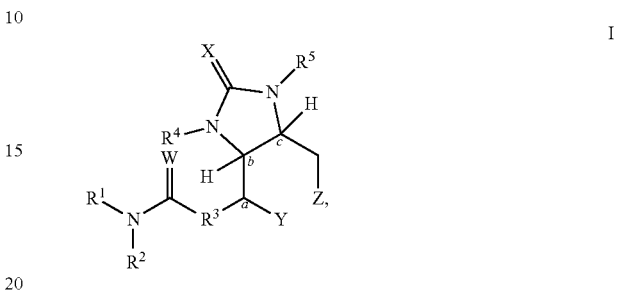

I or a salt thereof, wherein W can be S or O; X can be S, O, or NH; Y and Z can be H, or wherein Y and Z can be combined to form a S, O, or methylene; $R^1$ can be alkyl, alkenyl, alkynyl, aryl, heteroalkyl, heteroalkenyl, or heteroaryl; and wherein $R^1$ can further comprise a solid support; $R^2$ can be hydrogen or alkyl; $R^3$ can be alkyl, alkenyl, aryl, heteroalkyl, heteroalkenyl, heteroaryl, or arylalkyl; $R^4$ and $R^5$ can be independently hydrogen, alkyl, alkenyl, aryl, heteroalkyl, heteroalkenyl, heteroaryl, or arylalkyl; wherein at least one of $R^4$ and $R^5$ may not be hydrogen; and (a) can be a carbon center, wherein the carbon center can be in an R-configuration, an S-configuration, or can be a non-stereogenic center; and (b), and (c) can be carbon centers, wherein each of the carbon centers can be independently in the R-configuration or the S-configuration.

In some aspects are methods wherein the deprotecting of the subset of protected molecules can form the plurality of deprotected molecules, such that at least some of the molecules of the plurality of deprotected molecules or salts thereof independently have the structure:

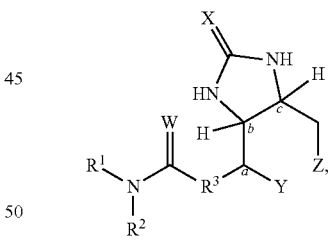

or a salt thereof, wherein W can be S or O; X can be S, O, or NH; Y and Z can be H, or wherein Y and Z can be combined to form a S, O, or methylene; $R^1$ can be alkyl, alkenyl, alkynyl, aryl, heteroalkyl, heteroalkenyl, or heteroaryl; and wherein $R^1$ can further comprise a solid support; $R^2$ can be hydrogen or alkyl; $R^3$ can be alkyl, alkenyl, aryl, heteroalkyl, heteroalkenyl, heteroaryl, or arylalkyl; (a) is be a carbon center, wherein the carbon center can be in an R-configuration, an S-configuration, or is a non-stereogenic center; and (b), and (c) are carbon centers, wherein each of the carbon centers can independently be in the R-configuration or the S-configuration.

In some aspects are methods wherein at least some of molecules of the plurality of protected molecules or salts thereof independently have the structure:

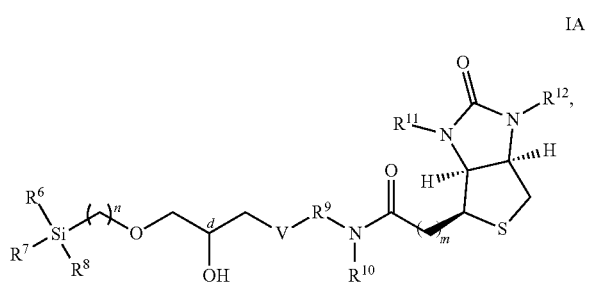

IA or a salt thereof, wherein V can be NH, O, S, or Se; n can be an integer with a value from 1-6, m can be an integer with a value from 1-6; $R^6$, $R^7$, and $R^8$ can be the same or different and can independently be hydrogen, alkyl, alkoxy, silyl, or siloxy, wherein at least one of $R^6$, $R^7$, and $R^8$ can further comprise a solid phase; $R^9$ can be alkyl, alkenyl, alkynyl or aryl, all optionally substituted with at least one of halo, alkyl, polyhaloalkyl, alkyoxy, haloalkoxy, polyhaloalkoxy, alkoxycarbonyl, alkenyl, alkynyl, cycloalkyl, cycloalkylalkyl, hydroxyl, hydroxyalkyl, nitro, cyano, amino, substituted amino, alkylamino, dialkylamino, thiol, alkylthio, alkylcarbonyl, acyl, alkoxycarbonyl, aminocarbonyl, alkylsulfinyl, sulfonamide, or sulfonyl; $R^{10}$ can be hydrogen or alkyl; $R^{11}$ and $R^{12}$ can independently be hydrogen or arylalkyl; wherein at least one of $R^{11}$ and $R^{12}$ may not be hydrogen; and (d) can be a carbon center, wherein the carbon center can be in the R-configuration or the S-configuration.

In some aspects are methods wherein at least some of molecules of the plurality of protected molecules or salts thereof independently have the structure:

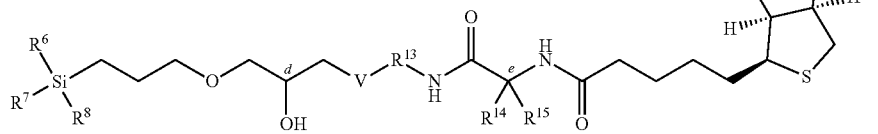

IB or a salt thereof, wherein V can be NH, O, S, or Se; $R^6$, $R^7$, and $R^8$ can be the same or different and can independently be hydrogen, alkyl, alkoxy, silyl, or siloxy, wherein at least one of $R^6$, $R^7$, and $R^8$ can further comprise a solid phase; $R^{13}$ can be alkyl, heteroalkyl, amino-substituted alkyl, amino-substituted heteroalkyl, amidoalkyl, amidoheteroalkyl, amino-substituted amidoheteroalkyl, each optionally substituted with at least one of alkyl, heteroalkyl, amino-substituted alkyl, amino-substituted heteroalkyl, amidoalkyl, amidoheteroalkyl, or amino-substituted amidoheteroalkyl; $R^{14}$ and $R^{15}$ can be the same or different and can independently be hydrogen, halo, alkyl, alkenyl, aryl, heteroalkyl, arylalkyl, hydroxyarylalkyl, heteroarylalkyl, cycloalkyl, thioalkyl, selenoalkyl, hydroxyalkyl, or amino-substituted alkyl; $R^{11}$ and $R^{12}$ can independently be hydrogen or arylalkyl, wherein at least one of $R^4$ and $R^5$ may not hydrogen; (d) is a carbon center, wherein the carbon center can be in the R-configuration or the S-configuration; and (e) is a second carbon center, wherein the second carbon center can be in the R-configuration, the S-configuration, or can be a non-stereogenic center. In some aspects, $R^{11}$ can be hydrogen and $R^{12}$ can be trityl, methoxytrityl, or dimethoxytrityl. In some aspects, $R^{13}$ can be ethylenediamino, (ethylenedioxy)bis (ethylamino), tris (2-aminoethyl)amino, polyamidoamino, or polyallylamino. In some aspects, $R^{14}$ and $R^{15}$ can be hydrogen. In some aspects, $R^{14}$ can be hydrogen and $R^{15}$ can be hydroxymethyl.

In some aspects, deprotecting can comprise a photodeprotection reaction. In some aspects, the photodeprotection reaction can comprise a photoacid or photoacid generator. In some aspects, detecting alignment can comprise binding a detectably labeled probe to the plurality of deprotected molecules. In some aspects, the detectably labeled probe can comprise a chromophoric dye. In some aspects, the labeled polypeptide can comprise streptavidin, neutravidin, or captavidin, or a salt of any of the above. In some aspects, the labeled polypeptide or salt thereof can be labeled with a chromophoric dye. In some aspects, the chromophoric dye can be a fluorescent dye or a phosphorescent dye.

In some aspects are methods wherein at least some of molecules of the plurality of protected molecules or salts thereof independently have the structure:

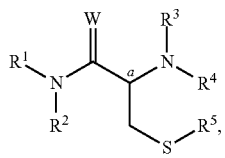

II or a salt thereof, wherein W can be S or O; $R^1$ is alkyl, alkenyl, alkynyl, aryl, heteroalkyl, heteroalkenyl, or heteroaryl; and wherein $R^1$ further comprises a solid support; $R^2$, $R^3$, and $R^4$ can independently be hydrogen or alkyl; $R^5$ can be alkyl, alkenyl, aryl, heteroalkyl, heteroalkenyl, heteroaryl, or arylalkyl; wherein (a) is a carbon center, wherein the carbon center can be in an R-configuration or an S-configuration; wherein deprotecting of the subset of the protected molecules forms a plurality of deprotected molecules that can comprise a sulfide, such that $R^5$ is hydrogen.

In some aspects are methods wherein the deprotecting of the subset of protected molecules or salts thereof can form the plurality of deprotected molecules or salts thereof, such that at least some of the molecules of the plurality of deprotected molecules or salts thereof independently have the structure:

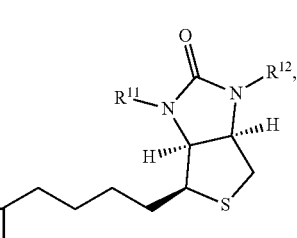

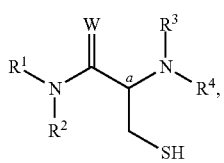

or a salt thereof, wherein W can be S or O; $R^1$ can be alkyl, alkenyl, alkynyl, aryl, heteroalkyl, heteroalkenyl, or heteroaryl; and wherein $R^1$ can further comprise a solid support; $R^2$, $R^3$, and $R^4$ can independently be hydrogen or alkyl; and wherein (a) is a carbon center, wherein the carbon center can be in an R-configuration or an S-configuration.

In some aspects are methods wherein at least some of molecules of the plurality of protected molecules or salts thereof independently have the structure:

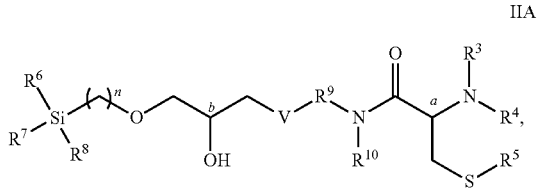

IIA or a salt thereof, wherein V can NH, O, S, or Se; n can be an integer with a value from 1-6; $R^3$ and $R^4$ can independently be hydrogen or alkyl; $R^5$ can be alkyl, alkenyl, aryl, heteroalkyl, heteroalkenyl, heteroaryl, or arylalkyl; $R^6$, $R^7$, and $R^8$ can be the same or different and are independently hydrogen, alkyl, alkoxy, silyl, or siloxy, wherein at least one of $R^6$, $R^7$, and $R^8$ can further comprise a solid phase; $R^9$ can be alkyl, alkenyl, alkynyl or aryl, all optionally substituted with at least one of halo, alkyl, polyhaloalkyl, alkyoxy, haloalkoxy, polyhaloalkoxy, alkoxycarbonyl, alkenyl, alkynyl, cycloalkyl, cycloalkylalkyl, hydroxyl, hydroxyalkyl, nitro, cyano, amino, substituted amino, alkylamino, dialkylamino, thiol, alkylthio, alkylcarbonyl, acyl, alkoxycarbonyl, aminocarbonyl, alkylsulfinyl, sulfonamide, or sulfonyl; $R^{10}$ can be hydrogen or alkyl; and (a) is a carbon center, wherein the carbon center can be in the R-configuration or the S-configuration; and (b) is a second carbon center, wherein the second carbon center can be in the R-configuration or the S-configuration.

In some aspects are methods wherein at least some of molecules of the plurality of protected molecules or salts thereof independently have the structure:

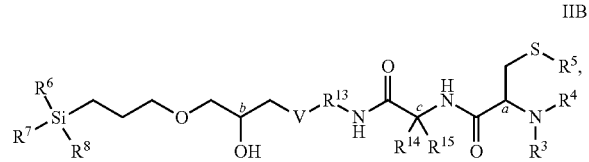

IIB or a salt thereof, wherein V can be NH, O, S, or Se; $R^3$ and $R^4$ can be independently hydrogen or alkyl; $R^5$ can be hydrogen or arylalkyl; $R^6$, $R^7$, and $R^8$ can be the same or different and can independently be hydrogen, alkyl, alkoxy, silyl, or siloxy, wherein at least one of $R^6$, $R^7$, and $R^8$ can further comprise a solid phase; $R^{13}$ can be alkyl, heteroalkyl, amino-substituted alkyl, amino-substituted heteroalkyl, amidoalkyl, amidoheteroalkyl, amino-substituted amidoheteroalkyl, each optionally substituted with at least one of alkyl, heteroalkyl, amino-substituted alkyl, amino-substituted heteroalkyl, amidoalkyl, amidoheteroalkyl, or amino-substituted amidoheteroalkyl, $R^{14}$ and $R^{15}$ can be the same or different and are independently hydrogen, halo, alkyl, alkenyl, aryl, heteroalkyl, arylalkyl, hydroxyarylalkyl, heteroarylalkyl, cycloalkyl, thioalkyl, selenoalkyl, hydroxyalkyl, or amino-substituted alkyl; (a) is a carbon center, wherein the carbon center can be in the R-configuration or the S-configuration; (b) is a second carbon center, wherein the second carbon center can be in the R-configuration or the S-configuration; and (c) is a third carbon center, wherein the third carbon center can be in the R-configuration, the S-configuration, or can be a non-stereogenic center. In some aspects, $R^5$ can be trityl, methoxytrityl, or dimethoxytrityl. In some aspects, $R^{13}$ can be ethylenediamino, (ethylenedioxy)bis(ethylamino), tris (2-aminoethyl)amino, polyamidoamino, or polyallylamino. In some aspects, $R^{14}$ and $R^{15}$ can be hydrogen. In some aspects, deprotecting can comprise a photodeprotection reaction. In some aspects, the photodeprotection reaction can comprise a photoacid or photoacid generator. In some aspects are methods wherein a deprotected molecule or salt thereof of the plurality of deprotected molecules or salts thereof can comprise a sulfide, and wherein the method can further comprise coupling the sulfide to a detectably labeled probe. In some aspects, the detectably labeled probe can comprise a chromophoric dye. In some aspects, the chromophoric dye can be a fluorescent dye. In some aspects, the fluorescent dye can be a maleimide dye.

In some aspects are methods wherein at least some of molecules of the plurality of protected molecules or salts thereof independently have the structure:

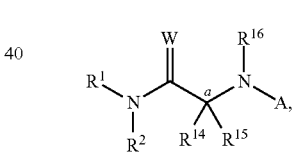

III or a salt thereof, wherein W can be S or O; $R^1$ can be alkyl, alkenyl, alkynyl, aryl, heteroalkyl, heteroalkenyl, or heteroaryl; and wherein $R^1$ can further comprise a solid support; $R^2$ can be hydrogen or alkyl; $R^{14}$ and $R^{15}$ can be the same or different and can independently be hydrogen, halo, alkyl, alkenyl, aryl, heteroalkyl, arylalkyl, hydroxyarylalkyl, heteroarylalkyl, cycloalkyl, thioalkyl, selenoalkyl, hydroxyalkyl, or amino-substituted alkyl; $R^{16}$ can be H or alkyl; A can be a functional group comprising a chromophore; and wherein (a) is a carbon center, wherein the carbon center can be in an R-configuration, an S-configuration, or can be a non-stereogenic center.

In some aspects, the deprotecting of the subset of the plurality of protected molecules can comprise contacting the subset of protected molecules with a reagent to form the plurality of deprotected molecules such that the plurality of deprotected molecules produces a lower fluorescent signal compared to the subset of protected molecules.

In some aspects, the deprotecting of the subset of the plurality of protected molecules can comprise contacting the subset of protected molecules with a reagent to form the plurality of deprotected molecules such that the plurality of deprotected molecules produces a higher fluorescent signal compared to the subset of protected molecules.

In some aspects are methods wherein at least some of molecules of the plurality of protected molecules or salts thereof independently have the structure:

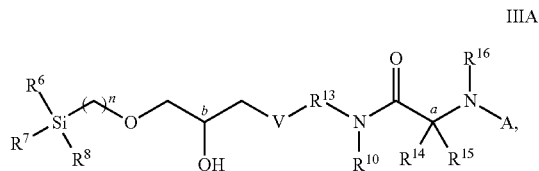

IIIA wherein V can be NH, O, S, or Se; n can be an integer with a value of 1-6; $R^6$, $R^7$, and $R^8$ can be the same or different and are independently hydrogen, alkyl, alkoxy, silyl, or siloxy; wherein at least one of $R^6$, $R^7$, and $R^8$ can further comprises a solid phase; $R^{10}$ and $R^{16}$ can independently be hydrogen or alkyl; $R^{13}$ can be alkyl, heteroalkyl, amino-substituted alkyl, amino-substituted heteroalkyl, amidoalkyl, amidoheteroalkyl, amino-substituted amidoheteroalkyl, each optionally substituted with at least one of alkyl, heteroalkyl, amino-substituted alkyl, amino-substituted heteroalkyl, amidoalkyl, amidoheteroalkyl, or amino-substituted amidoheteroalkyl; $R^{14}$ and $R^{15}$ can be the same or different and are independently hydrogen, halo, alkyl, alkenyl, aryl, heteroalkyl, arylalkyl, hydroxyarylalkyl, heteroarylalkyl, cycloalkyl, thioalkyl, selenoalkyl, hydroxyalkyl, or amino-substituted alkyl; A can be a functional group comprising a chromophore; and (a) is a carbon center, wherein the carbon center can be in the R-configuration or the S-configuration, or can be a non-stereogenic center; (b) is a second carbon center, wherein the second carbon center is in the R-configuration, the S-configuration. In some aspects, the chromophore can be a fluorescent chromophore or a phosphorescent chromophore. In some aspects, $R^{13}$ can be ethylenediamino, (ethylenedioxy)bis(ethylamino), tris(2-aminoethyl)amino, polyamidoamino, or polyallylamino. In some aspects, $R^{14}$ and $R^{15}$ can be hydrogen. In some aspects, the reagent can comprise an acid. In some aspects are methods wherein the chromophore is degraded. In some aspects are methods wherein the reagent comprises ultraviolet light. In some aspects, the chromophore is photobleached.

Also disclosed herein are methods further comprising forming a first array region, comprising: (a) forming an oxygen-silicon covalent bond between a solid substrate and a first molecule or salt thereof comprising: (i) a silicon at a first end and an epoxide at a second end; (b) forming a V-carbon covalent bond between a carbon atom of said epoxide and a second molecule or salt thereof comprising an amino group, thereby opening the epoxide; wherein V can be nitrogen, oxygen, sulfur, or selenium; wherein said epoxide and said silicon can be linked by a group comprising an alkyl, alkylether, or alkylthioether, wherein each of alkyl, alkylether, or alkylthioether can optionally be substituted with hydroxyl, thiol, amino, or halo. In some aspects, the first molecule or salt thereof can be 3-glycidoxypropyltrimethoxysilane (GPTMS) or a salt thereof. In some aspects, the second molecule or salt thereof can be ethylenediamine (EDA), (ethylenedioxy)bis(ethylamine) (EDBA), tris(2-aminoethyl)amine (TAEA), polyamidoamine (PAMAM), or polyallylamine (PAAm), or a salt of any of the above. In some aspects, the second molecule or salt thereof can be PAAm or a salt thereof. In some aspects, the said PAAm or salt thereof can have a weight average molecular weight of from about 1 KDa to about 100 KDa. In some aspects are methods further comprising coupling the amino group to a protected amino acid or salt thereof. In some aspects, the protected amino acid or salt thereof is a tert-butyl carbamate (Boc)- or 9-fluorenylmethyl carbamate (Fmoc)-protected amino acid or salt thereof. In some aspects, the amino acid can be glycine or a salt thereof. In some aspects, the amino acid can be serine or a salt thereof. In some aspects are methods further comprising deprotecting the protected amino acid or salt thereof. In some aspects are methods further comprising coupling the amino acid or salt thereof to: a protected biotin or salt thereof; or a protected serine or salt thereof; or a chromophoric dye, to form the plurality of protected molecules. In some aspects, the chromophoric dye can be a fluorescent dye or a phosphorescent dye. In some aspects, detecting alignment can further comprise a fluorescence scan. In some aspects, methods described herein further comprise determining alignment. In some aspects, determining alignment can comprise determining alignment of a center of the first array region and a center of the second array region, wherein substantial alignment of the center of the first array region with the center of the second array region indicates proper alignment of a photolithographic mask. In some aspects, determining alignment can comprise determining the uniformity of distance from a boundary of the first array region to a boundary of the second array region, wherein a substantially uniform distance from the boundary of the first array region to the boundary of second array region indicates proper alignment of a photolithographic mask.

Also disclosed herein are molecules or salts thereof having the structure I, or a salt thereof, wherein W can be S or O; X can be S, O, or NH; Y and Z can be H, or wherein Y and Z are combined to form a S, O, or methylene; $R^1$ can be alkyl, alkenyl, alkynyl, aryl, heteroalkyl, heteroalkenyl, or heteroaryl; and wherein $R^1$ can further comprise a solid support; $R^2$ can be hydrogen or alkyl; $R^3$ can be alkyl, alkenyl, aryl, heteroalkyl, heteroalkenyl, heteroaryl, or arylalkyl; $R^4$ and $R^5$ can be independently hydrogen or alkyl, alkenyl, aryl, heteroalkyl, heteroalkenyl, heteroaryl, or arylalkyl; wherein at least one of $R^4$ and $R^5$ is not hydrogen; and (a) is a carbon center, wherein the carbon center can be in an R-configuration, an S-configuration, or can be a non-stereogenic center; (b), and (c) are carbon centers, wherein each of the carbon centers can independently be in the R-configuration or the S-configuration; and wherein the deprotecting of the subset of the protected molecules can form the plurality of deprotected molecules such that $R^4$ and $R^5$ are hydrogen.

Also disclosed herein are molecules or salts thereof having the structure IA, or a salt thereof, wherein Y can be NH, O, S, or Se; n can be an integer having a value of 1-6, m can be an integer having a value of 1-6; $R^6$, $R^7$, and $R^8$ can be the same or different and can independently be hydrogen, alkyl, alkoxy, silyl, or siloxy, wherein at least one of $R^6$, $R^7$, and $R^8$ can further comprise a solid phase; $R^9$ can be alkyl, alkenyl, alkynyl or aryl, all optionally substituted with at least one of halo, alkyl, polyhaloalkyl, alkyoxy, haloalkoxy, polyhaloalkoxy, alkoxycarbonyl, alkenyl, alkynyl, cycloalkyl, cycloalkylalkyl, hydroxyl, hydroxyalkyl, nitro, cyano, amino, substituted amino, alkylamino, dialkylamino, thiol, alkylthio, alkylcarbonyl, acyl, alkoxycarbonyl, aminocarbonyl, alkylsulfinyl, sulfonamide, or sulfonyl; $R^{10}$ can be hydrogen or alkyl; $R^{11}$ and $R^{12}$ can be independently hydrogen or arylalkyl; wherein at least one of $R^{11}$ and $R^{12}$ is not hydrogen; and (d) is a carbon center, wherein the carbon center can be in the R-configuration or the S-configuration, or wherein the protected molecules or salts thereof can comprise a mixture of the R-configuration and the S-configuration.

Also disclosed herein are molecules or salts thereof having the structure IB, or a salt thereof, wherein Y can be NH, O, S, or Se; $R^6$, $R^7$, and $R^8$ can be the same or different and can independently be hydrogen, alkyl, alkoxy, silyl, or siloxy, wherein at least one of $R^6$, $R^7$, and $R^8$ can further comprise a solid phase; $R^{13}$ can be alkyl, heteroalkyl, amino-substituted alkyl, amino-substituted heteroalkyl, amidoalkyl, amidoheteroalkyl, amino-substituted amidoheteroalkyl, each optionally substituted with at least one of alkyl, heteroalkyl, amino-substituted alkyl, amino-substituted heteroalkyl, amidoalkyl, amidoheteroalkyl, or amino-substituted amidoheteroalkyl; $R^{14}$ and $R^{15}$ can be the same or different and can independently be hydrogen, halo, alkyl, alkenyl, aryl, heteroalkyl, arylalkyl, hydroxyarylalkyl, heteroarylalkyl, cycloalkyl, thioalkyl, selenoalkyl, hydroxyalkyl, or amino-substituted alkyl; $R^{11}$ and $R^{12}$ can independently be hydrogen or arylalkyl, wherein at least one of $R^4$ and $R^5$ is not hydrogen; (d) is a carbon center, wherein the carbon center can be in the R-configuration or the S-configuration, or wherein the protected molecules or salts thereof can comprise a mixture of the R-configuration and the S-configuration; and (e) is a second carbon center, wherein the second carbon center can be in the R-configuration, the S-configuration, or can be a non-stereogenic center. In some aspects, $R^{11}$ can be hydrogen and $R^{12}$ can be dimethoxytrityl. In some aspects, $R^{13}$ can be ethylenediamino, (ethylenedioxy)bis(ethylamino), tris(2-aminoethyl) amino, polyamidoamino, or polyallylamino. In some aspects, $R^{14}$ and $R^{15}$ can be hydrogen. In some aspects, $R^{14}$ can be hydrogen and $R^{15}$ can be hydroxymethyl.

Also disclosed herein are molecules or salts thereof having the structure II, or a salt thereof, wherein W can be S or O; $R^1$ can be alkyl, alkenyl, alkynyl, aryl, heteroalkyl, heteroalkenyl, or heteroaryl; and wherein $R^1$ further comprises a solid support; $R^2$, $R^3$, and $R^4$ can be independently hydrogen or alkyl; $R^5$ can be alkyl, alkenyl, aryl, heteroalkyl, heteroalkenyl, heteroaryl, or arylalkyl; and wherein (a) is a carbon center, wherein the carbon center can be in an R-configuration or an S-configuration.

Also disclosed herein are molecules or salts having the structure IIA, or a salt thereof, wherein V can be NH, O, S, or Se; n can be an integer having a value from 1-6; $R^3$ and $R^4$ can independently be hydrogen or alkyl; $R^5$ can be alkyl, alkenyl, aryl, heteroalkyl, heteroalkenyl, heteroaryl, or arylalkyl; $R^6$, $R^7$, and $R^8$ can be the same or different and are independently hydrogen, alkyl, alkoxy, silyl, or siloxy, wherein at least one of $R^6$, $R^7$, and $R^8$ further comprises a solid phase; $R^9$ can be alkyl, alkenyl, alkynyl or aryl, all optionally substituted with at least one of halo, alkyl, polyhaloalkyl, alkyoxy, haloalkoxy, polyhaloalkoxy, alkoxycarbonyl, alkenyl, alkynyl, cycloalkyl, cycloalkylalkyl, hydroxyl, hydroxyalkyl, nitro, cyano, amino, substituted amino, alkylamino, dialkylamino, thiol, alkylthio, alkylcarbonyl, acyl, alkoxycarbonyl, aminocarbonyl, alkylsulfinyl, sulfonamide, or sulfonyl; $R^{10}$ can be hydrogen or alkyl; and (a) is a carbon center, wherein the carbon center can be in the R-configuration or the S-configuration; and (b) is a second carbon center, wherein the second carbon center can be in the R-configuration or the S-configuration, or wherein the protected molecules or salts thereof can comprise a mixture of the R-configuration and the S-configuration.

Also described herein are molecules or salts thereof having the structure IIB, or a salt thereof, wherein V can be NH, O, S, or Se; $R^3$ and $R^4$ can independently be hydrogen or alkyl; $R^5$ can be hydrogen or arylalkyl; $R^6$, $R^7$, and $R^8$ can be the same or different and can independently be hydrogen, alkyl, alkoxy, silyl, or siloxy, wherein at least one of $R^6$, $R^7$, and $R^8$ can further comprises a solid phase; $R^{13}$ can be alkyl, heteroalkyl, amino-substituted alkyl, amino-substituted heteroalkyl, amidoalkyl, amidoheteroalkyl, amino-substituted amidoheteroalkyl, each optionally substituted with at least one of alkyl, heteroalkyl, amino-substituted alkyl, amino-substituted heteroalkyl, amidoalkyl, amidoheteroalkyl, or amino-substituted amidoheteroalkyl; $R^{14}$ and $R^{15}$ can be the same or different and can independently be hydrogen, halo, alkyl, alkenyl, aryl, heteroalkyl, arylalkyl, hydroxyarylalkyl, heteroarylalkyl, cycloalkyl, thioalkyl, selenoalkyl, hydroxyalkyl, or amino-substituted alkyl; (a) is a carbon center, wherein the carbon center can be in the R-configuration or the S-configuration; (b) is a second carbon center, wherein the second carbon center can be in the R-configuration or the S-configuration, or wherein the protected molecules or salts thereof can comprise a mixture of the R-configuration and the S-configuration; and (c) is a third carbon center, wherein the third carbon center can be in the R-configuration, the S-configuration, or can a non-stereogenic center.

Also disclosed herein are molecules or salts thereof having the structure III, or a salt thereof, wherein W is S or O; $R^1$ can be alkyl, alkenyl, alkynyl, aryl, heteroalkyl, heteroalkenyl, or heteroaryl; and wherein $R^1$ can further comprises a solid support; $R^2$ can be hydrogen or alkyl; $R^{14}$ and $R^{15}$ are the same or different and are independently hydrogen, halo, alkyl, alkenyl, aryl, heteroalkyl, arylalkyl, hydroxyarylalkyl, heteroarylalkyl, cycloalkyl, thioalkyl, selenoalkyl, hydroxyalkyl, or amino-substituted alkyl; $R^{16}$ can be H or alkyl; A can be a functional group comprising a chromophore; and wherein (a) can be a carbon center, wherein the carbon center can be in an R-configuration, an S-configuration, or can be a non-stereogenic center. In some aspects, the chromophore can be a fluorescent chromophore or a phosphorescent chromophore.

Also disclosed herein are molecules or salts thereof having the structure IIIA, or a salt thereof, wherein V can be NH, O, S, or Se; n can be an integer having a value of 1-6, m can be an integer having a value of 1-6; $R^6$, $R^7$, and $R^8$ can be the same or different and can independently be hydrogen, alkyl, alkoxy, silyl, or siloxy, wherein at least one of $R^6$, $R^7$, and $R^8$ can further comprises a solid phase; $R^{10}$ and $R^{16}$ can independently be hydrogen or alkyl; $R^{13}$ can be alkyl, heteroalkyl, amino-substituted alkyl, amino-substituted heteroalkyl, amidoalkyl, amidoheteroalkyl, amino-substituted amidoheteroalkyl, each optionally substituted with at least one of alkyl, heteroalkyl, amino-substituted alkyl, amino-substituted heteroalkyl, amidoalkyl, amidoheteroalkyl, or amino-substituted amidoheteroalkyl; $R^{14}$ and $R^{15}$ can be the same or different and can independently be hydrogen, halo, alkyl, alkenyl, aryl, heteroalkyl, arylalkyl, hydroxyarylalkyl, heteroarylalkyl, cycloalkyl, thioalkyl, selenoalkyl, hydroxyalkyl, or amino-substituted alkyl; and (a) is a carbon center, wherein the carbon center can be in the R-configuration or the S-configuration, or can be a non-stereogenic center; and (b) is a second carbon center, wherein the second carbon center can be in the R-configuration, the S-configuration, or wherein the protected molecules or salts thereof can comprise a mixture of the R-configuration and the S-configuration.

Also disclosed herein are arrays comprising a plurality of the molecules or salts of structures I, IA, IB, II, IIA, IIB, III, or IIIA. In some aspects, the arrays can further comprise at least two peptide features. In some aspects, at least two of the plurality of molecules or salts thereof can be cross-linked. In some aspects, the arrays can further comprise instructions for use. Also disclosed herein are methods of making arrays comprising any of the methods disclosed herein. In some aspects, making an array can comprise associating the molecules or salt of structures I, IA, IB, II, IIA, IIB, III, or IIIA with a substrate. Also disclosed herein are kits. In some aspects, kits can comprise the molecules or salts of structures I, IA, IB, II, IIA, IIB, III, or IIIA. In some aspects, kits can further comprise instructions for use. Also disclosed herein are methods of making kits. In some aspects, making kits can comprise forming the kit with the molecule or salt of any of the structures I, IA, IB, II, IIA, IIB, III, or IIIA. Also disclosed herein are molecules or salts thereof made by any of the methods disclosed herein.

Also described herein are chips or wafers made by any of the methods described herein. Also described herein are slides made by any of the methods described herein. Also described herein are arrays made by any of the methods described herein.

INCORPORATION BY REFERENCE

All publications, patents, and patent applications herein are incorporated by reference in their entireties. In the event of a conflict between a term herein and a term in an incorporated reference, the term herein controls.

BRIEF DESCRIPTION OF THE DRAWINGS

The novel features described herein are set forth with particularity in the appended claims. A better understanding of the features and advantages of the features described herein will be obtained by reference to the following detailed description that sets forth illustrative examples, in which the principles of the features described herein are utilized, and the accompanying drawings of which:

DETAILED DESCRIPTION

Figure 1:
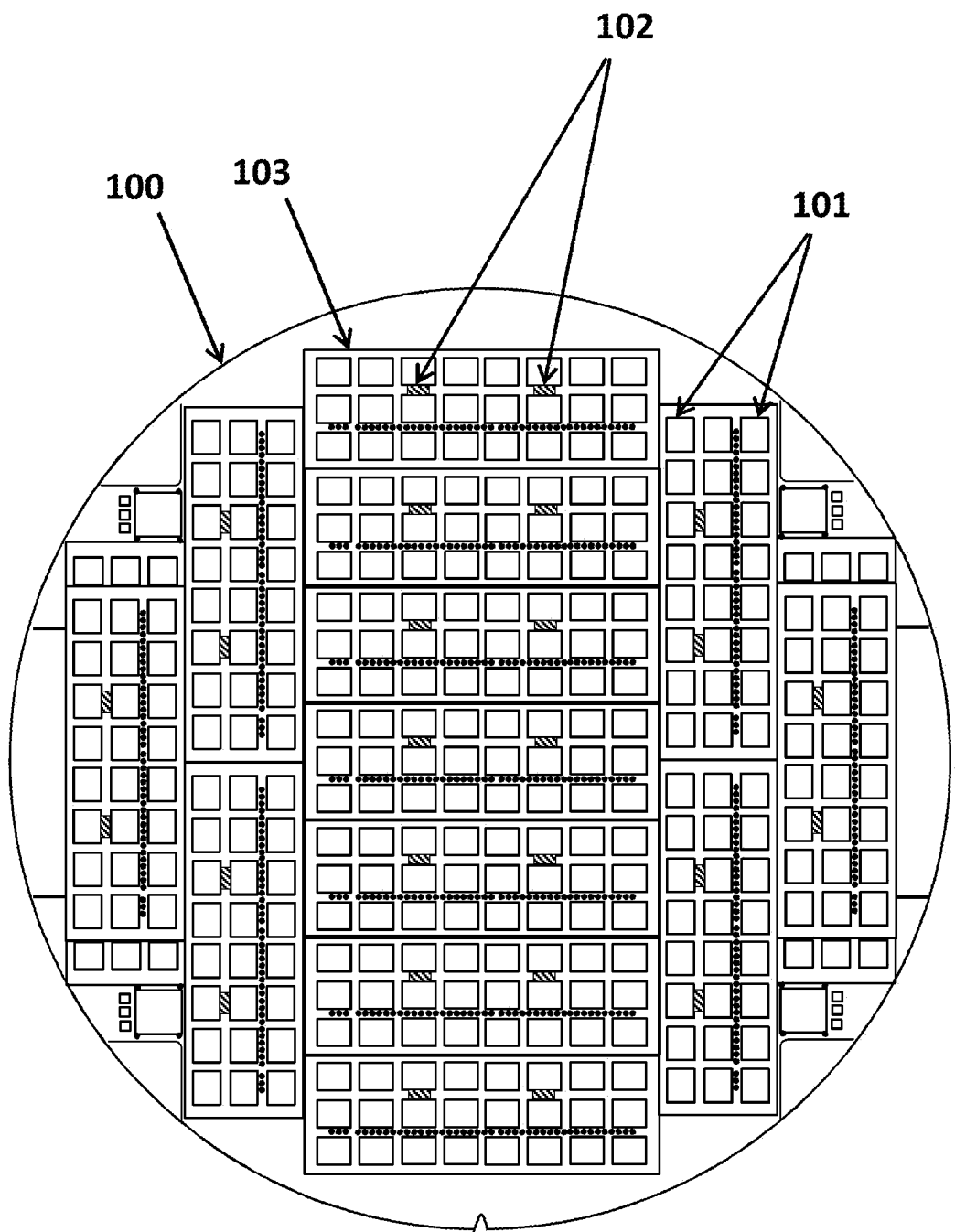
FIG. 1 illustrates a wafer with arrays and alignment controlling regions.

Several aspects are described below with reference to example applications for illustration. It should be understood that numerous specific details, relationships, and methods are set forth to provide a full understanding of the features described herein. One having ordinary skill in the relevant art, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" can mean within an acceptable error range for the particular value as determined by one of ordinary skill in the art, which will depend in part on how the value is measured or determined, i.e. the limitations of the measurement system. For example, "about" can mean within 1 or more than 1 standard deviation. Alternatively, "about" can mean a range of up to 20%, up to 10%, up to 5%, or up to 1% of a given value. Alternatively, particularly with respect to biological systems or processes, the term can mean within an order of magnitude, within 5-fold, and more preferably within 2-fold, of a value. Where particular values are described in the application and claims, unless otherwise stated the term "about" meaning within an acceptable error range for the particular value should be assumed. The term "about" has the meaning as commonly understood by one of ordinary skill in the art. In some embodiments, the term "about" refers to ±10%. In some embodiments, the term "about" refers to ±5%.

Overview

Detecting and diagnosing immune-mediated disorders, including autoimmune disorders, infections, and cancer, is challenging, with patients having a difficult time receiving an accurate or correct diagnosis. In many instances, patients are often misdiagnosed with other autoimmune conditions because of the closely related nature of these diseases. The disclosure, in one aspect, relates to compounds, methods, and devices that identify differential patterns of peripheral-blood antibody binding to an array-bound molecular library. Differential binding of patient samples to the array results in specific binding patterns or signatures indicative of the disease state of the patient. These binding signatures can accurately determine or diagnose a disease activity, including but not limited to autoimmune disease activity, infectious disease activity, cancer activity, and diabetes disease activity. The identification of such differential binding activity, or signature, is referred to as "immunosignaturing." Synthesized peptide libraries have been commonly used for antibody binding characterization. However, protein and robotically printed peptide arrays have been cost-prohibitive and in situ synthesized peptide arrays have suffered from lack of scalability, poor reproducibility and low production quality. The technologies herein, in one aspect, will enable reliable, low cost, and scalable methods for construction and use of arrays for immunosignaturing assays.

In some embodiments, arrays with chemical libraries produced by the technologies disclosed herein are used for immune-based diagnostic assays, for example, immunosignature assays. In one aspect, using a patient's antibody repertoire from a drop of blood bound to the arrays, a fluorescence binding profile image of the bound array provides sufficient information to identify and classify a disease state. The arrays disclosed herein incorporate analytical measurements capability within each synthesized array using orthogonal analytical methods including ellipsometry, mass spectrometry, and fluorescence. These measurements enable longitudinal qualitative and quantitative assessment of array synthesis performance.

New platforms are disclosed herein to dramatically increase the number of detected therapeutic antibody interactions, which may reduce this risk of undetected off-target effects. The technologies are based on merged peptide synthesis chemistry with semiconductor manufacturing processes by utilizing mask-based photolithography to pattern, in situ, libraries containing more than 40 million peptides (potential epitopes) on an eight-inch wafer. This wafer can be diced into 13 microscope-slide dimensioned chips for downstream analysis. With such a peptide library chips described herein, antibody binding profile assays can be scaled to more than 10 million antibody-target interactions per day at a fraction of the cost of current antibody characterization platforms. Antibody epitope point-variant analysis demonstrates the applicability of the peptide chips to antibody characterization.

In some embodiments, the array is a wafer-based, photolithographic, in situ peptide array produced using reusable masks and automation to obtain arrays of scalable numbers of combinatorial sequence peptides. In some embodiments, the peptide array comprises at least 5,000, at least 10,000, at least 15,000, at least 20,000, at least 30,000, at least 40,000, at least 50,000, at least 100,000, at least 200,000, at least 300,000, at least 400,000, at least 500,000, at least 1,000,000, at least 2,000,000, at least 3,000,000, at least 4,000,000, at least 5,000,000, at least 10,000,000, at least 100,000,000 or more peptides having different sequences. Multiple copies of each of the different sequence peptides can be situated on the wafer at addressable locations known as features.

The technologies disclosed herein include a photolithographic array synthesis platform to produce array-based libraries on silicon wafers. In one aspect, the platform comprises a substrate on which to perform peptide synthesis. Applying a photolithographic mask, followed by UV light allows for peptide synthesis by blocking the application of UV light to all parts of substrate surface except for the particular region where photocatalytic chemistry is desired. Further, by sequentially applying another mask with UV light exposure, various array features can be established. By utilizing photolithographic feature patterning, the array synthesis platform is highly-scalable and capable of producing combinatorial chemical libraries with 40 million features on an 8-inch wafer. Photolithographic array synthesis is performed using semiconductor wafer production equipment in a class 10,000 cleanroom to achieve high reproducibility. When the wafer is diced into standard microscope slide dimensions, each slide contains more than 3 million distinct chemical entities.

In some embodiments, a first mask has one or more openings on desired feature locations, where one or more types of monomers or polymers can be deposited to the feature locations. Then, the first mask is removed and a second mask is applied. The second mask may be different from the first mask. The second mask may have one or more openings overlapping with, but not identical to, the opening(s) of the first mask. In some cases, the second mask has one or more openings not overlapping with any opening of the first mask. Once the second mask is applied, one or more types of monomers or polymers can be deposited to the feature locations. The monomers or polymers used in the second step may be different from those used in the first step. When repeating this process, an array of various features can be established.

In some embodiments, construction of peptide features on an array poses some challenges that can be addressed by the technologies disclosed herein. In one aspect, the technologies disclosed herein address the problem of mask alignment. When applying a mask, the alignment of the mask with the desired feature locations is important because misalignment can cause monomers or polymer to be deposited at an incorrect location, introducing errors in the synthesized array features. Described herein are methods and compositions which allow detection of misalignment at any step of masking (e.g., any step of polymer synthesis).

Figure 2:
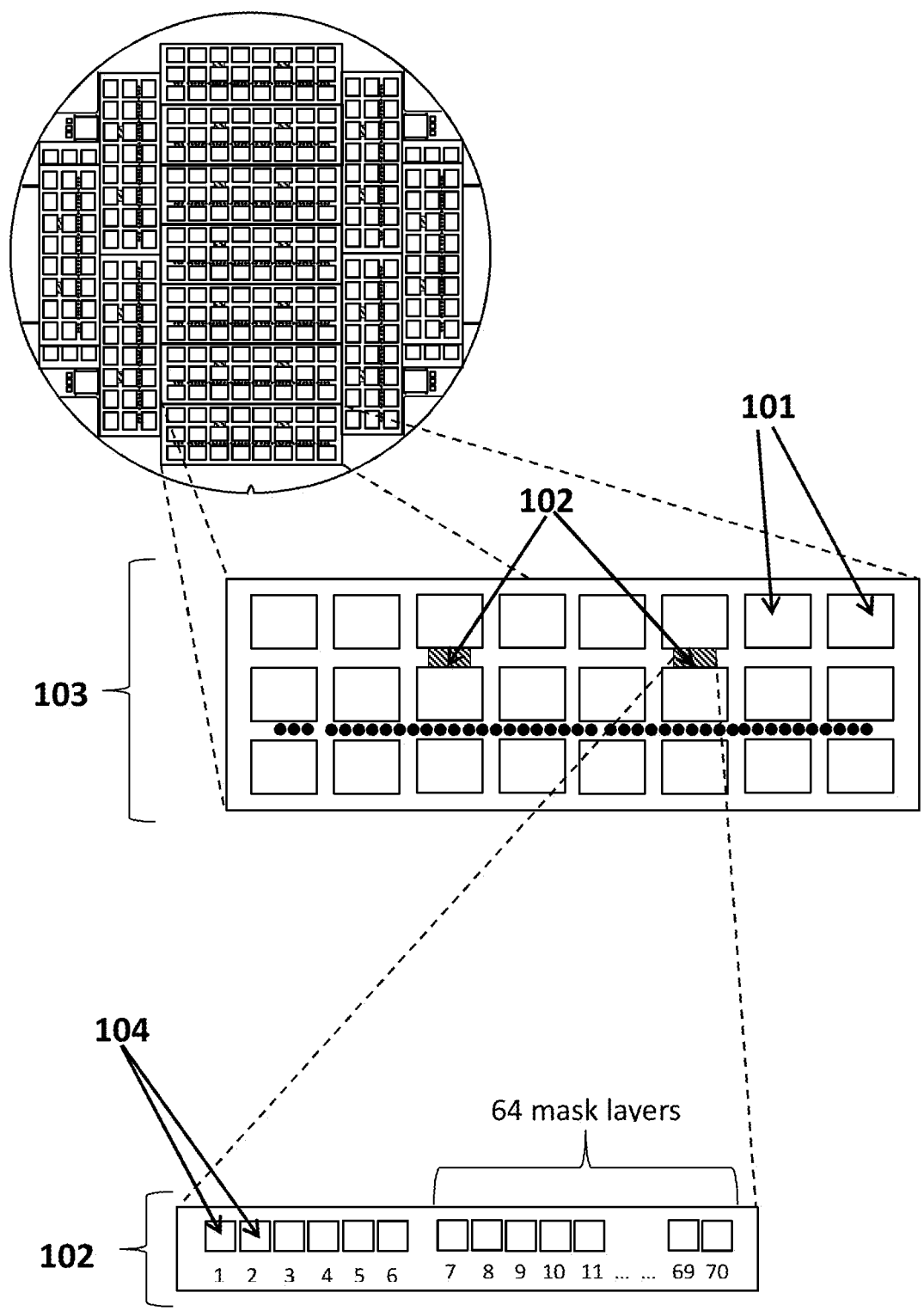
FIG. 2 illustrates alignment controlling spots.

The technologies disclosed herein utilize special locations as controlling spots to align the masks. Referring to FIG. 1, a substrate 100 is used to manufacture one or more slides 103 of arrays. Slides often comprise multiple squares 101. In some embodiments, a slide comprises a barcode, wherein a barcode identifies a slide or square 101. Each square (e.g., 101) may be an array. Often, squares 101 comprise a synthesis site for the generation of polymers, such as peptides. On the substrate 100, alignment control may be based on a plurality of inter-array or inter-feature regions 102. The number of the alignment controlling regions may depend on the design of a fabrication process. In some instances, the substrate 100 is a wafer. In some embodiments, a wafer substrate comprises a plurality of slides of arrays. In some aspects, a wafer substrate may comprise 1, 2, 3, 4, 5, 6, 7, 8, 9, 10, 11, 12, 13, 14, 15, 16, 17, 18, 19, or 20 or more slides. A slide may contain 1, 2, 3, 4, 5, 6, 7, 8, 9, or 10 or more alignment control regions. Each region may comprise a plurality of controlling spots; the number of controlling spots depends on the fabrication design. In some aspects, the alignment control region may comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 80, 190, 200, 300, 400, 500, 600, 700, 800, 900, or 1000 or more spots 104 (FIG. 2). For example, referring to FIG. 2, a region may contain 70 spots (numbered 1, 2, 3, . . . , 70). In some embodiments, the alignment control region can have dimensions ranging from 1 µm-1000 µm×1 µm-1000 µm. In some embodiments, the alignment control region can have dimensions ranging from 10 µm-100 µm×10 µm-100 µm. In some embodiments, the alignment control region can have dimensions of about 34 µm× about 20 µm in size. In some embodiments, a spot can correspond to a mask. In the example of FIG. 2, out of the 70 spots, 64 spots (numbered 7, 8, 9, . . . , 70) correspond to 64 mask layers of the full synthesis. In some instances, two or more spots are used as controls to check misalignments that are approximately one full spot misaligned (not "in-frame", e.g., mask is aligned to spots 2 and 5, but not aligned to desired spots 1 and 4). In an exemplary arrangement, spots 1 and 4 are exposed to all reagents, and a quality control mask.

Figure 3:
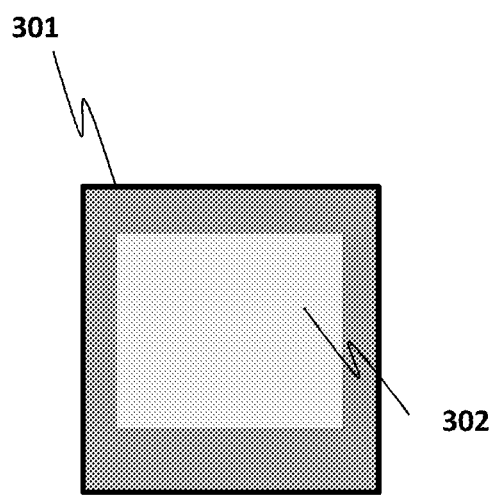
FIG. 3 illustrates an exemplary box and frame of an alignment controlling spot.

Referring to FIG. 3, each controlling spot comprises a frame region 301 and a box region 302. During the manufacturing process, the frame region 301 can be deposited with a first type of compound. In some embodiments, the box region 302 can be further deposited with a second type of compound. In some embodiments, the box region 302 can be formed by removing the first type of compound within the box region 302. In some embodiments, the box region 302 can be formed by chemically modifying the first type of compound within the box region 302. In some embodiments, forming the frame region comprises a first photolithographic mask and forming the box region comprises a second photolithographic mask. Various compounds may be used herein; details are described below. Determining alignment of a box region within the frame region allows a determination of proper or improper photolithographic mask alignment. When a photolithographic mask is properly aligned, the box region will be centered within the frame region. When a photolithographic mask is improperly aligned, the box region will not be centered within the frame region.

Determining alignment of the box region within the frame region can be accomplished by various means. In some embodiments, a box region will be properly aligned within a frame region when center of the box region is substantially aligned with the center of the frame region. In some embodiments, a box region will be properly aligned within a frame region when there is a substantially uniform distance from the boundary of the box region to the boundary of the frame region.

Alignment determination at one or more spots corresponding to one or more masking steps is often utilized to verify that monomers were deposited onto the correct areas of an array during a masking step. Various actions are taken as a result of an improperly aligned mask. In some instances, an improperly aligned mask is corrected by re-alignment of the mask with the frame region. After re-alignment, in some cases an additional alignment check is performed and the process is repeated until the alignment is correct. Alignments are optionally checked before or after a polymer synthesis extension step. For example, alignment determination of one or more spots results in a determination that a mask is misaligned; the mask is then realigned, and alignment is checked again. If the alignment is determined to be acceptable, a mask is applied to desired polymer synthesis regions, and polymer mummers are added to extend the polymers on the array. If the mask cannot be aligned, in some cases the array is discarded. In some embodiments, determination of alignment is used as a quality control check. In some cases, analysis of spots is used to determine which monomers were not added properly due to a misaligned mask. Alignment determinations are optionally made before, during or after any cycles of polymer synthesis in the array. In some instances, an improperly aligned mask results in recordation of the misalignment and time (or which monomer step was misaligned), and optionally later review or evaluation. In some instances, an improperly aligned mask results in aborting further masking steps. In some instances, polymers synthesized with misaligned masks are discarded. Other actions may be taken as a result of misalignment, and will vary depending on the desired application of the methods and compositions described herein.

Determination of alignment may be measured through various means of comparing a box region to a frame region. Alignment is in some instances represented as a threshold value (e.g., greater than 5% misaligned is a misalignment). Alignment is in some instances represented on a continuum (e.g., 5% misaligned). For example, the distance between all edges of a box region and all edges of the frame region are substantially uniform when the mask is aligned. Alignments may be determined by measuring the distance between a box region edge and the closest frame region edge. For example, for a box measuring 28×14 μm and a frame measuring 34×20 μm perfect alignment corresponds to a 6 μm "perfect distance" between each edge of the box region to the closest edge of the frame region. In some instances, the mask is aligned when the distance between each edge of the box region to the closest edge of the frame region is within about 0.01%, 0.1%, 1%, 2%, 3%, 5%, 10%, 15%, 20%, 25%, 30%, 40%, 50%, 60%, 70%, 80%, 90%, or 100% of a perfect alignment distance. Determination of alignment is often measured through the distance between the center of the box region and the edges of the frame region are uniform. For example, the mask is aligned when the distance from the center of the box region to the edges of the frame region are within about 0.01%, 0.1%, 1%, 2%, 3%, 5%, 10%, 15%, 20%, 25%, 30%, 40%, 50%, 60%, 70%, 80%, 90%, or 100% of the distance from the center of the box region to the edges of the frame region in a perfect alignment. In some embodiments, the intensity of fluorescence is also used to measure alignment. Additional methods of determining correct alignment between the box and frame regions are also consistent with the disclosure. An alignment determination may be made by comparing the largest distance between an edge of the box region and an edge of the frame region, with the shortest distance between an edge of the box region and an edge of the frame region. In some cases, a mask is aligned when the difference between the largest distance between an edge of the box region and an edge of the frame region and the shortest distance between an edge of the box region and an edge of the frame region is within about 0.01%, 0.1%, 1%, 2%, 3%, 5%, 10%, 15%, 20%, 25%, 30%, 40%, 50%, 60%, 70%, 80%, 90%, or 100% of the average of the largest distance between an edge of the box region and an edge of the frame region and the shortest distance between an edge of the box region and an edge of the frame region.

Further described herein are devices, systems, and methods for visualizing alignments. In some instances, devices are imaging instruments capable of obtaining images of samples such as wafers, slides, and/or spots for measuring alignment. Such imaging instruments often comprise at least one component such as a source, a detector, a computer system, a device for displaying acquired images, or other component used for imaging purposes. In some instances, an imaging instrument further comprises a fluidics system, capable of adding or removing reagents from the sample. In some instances, the imaging instrument is a microscope, such as a fluorescence microscope. In some instances, the imaging instrument is an ImageXpress Micro XLS Widefield High Content Screening System. In some cases, the imaging instrument is an Innopsys 910/910AL or 1100/1100AL. In some embodiments, the imaging instrument comprises a laser raster-based system. Often, the imaging instrument comprises an X-Y sample stage and a Z focus stage. In some embodiments, the stages have a resolution such as at least 200 nm, or at least 1 nm, 10 nm, 20 nm, 30, 50 nm, 75 nm, 100 nm, or at least 150 nm. In some cases, an imaging instrument can capture fluorescent light at a plurality of wavelengths. In some cases, an imaging instrument can capture fluorescent light at a plurality of wavelengths using more than one fluorescent channel.

Imaging instrument sources variously comprise LEDs, lamps, Light Guide Illumination, laser, or other energy source which facilitates detection of mask alignment. Often, a lamp is a halogen lamp, Hg lamp, Xenon lamp, or other source of electromagnetic radiation. In some embodiments, instrument sources are capable of generating multiple wavelengths of light. Detectors comprise various components known in the art, including but are not limited to CCD cameras, CMOS detectors, photomultiplier tubes, fluorescence detectors, radiation/isotope detectors, or other detector capable of detecting masking alignment. Detectors in some embodiments comprise one or more filters, such as a TRITC-B filter cube. In some embodiments, detectors are capable of detecting multiple wavelengths of light, optionally simultaneously through one or more channels. In some instances, the detector comprises a wide field of view camera. Such cameras are capable of various magnification levels, such as at least 1-100×. In some instances, the magnification level is or at least 1×, 2×, 3×, 4×, 5×, 10×, 15×, 20×, 25×, 30×, 50×, 75×, 90×, or 100× magnification. Such cameras are in some cases capable of having various numerical aperture, such as 0.05-0.95. In some instances, a camera has a numerical aperture of at least 0.05, 0.1, 0.2, 0.3, 0.4, 0.5, 0.6, 0.7, 0.8, 0.9, or at least 0.95 numerical aperture. Computer systems include hardware, software, memory storage, networking interfaces, monitors, or other component. Computers in some embodiments are configured to control, process, and analyze samples and alignment data during alignment determinations. Computer software is in some instances used to process or refine alignment data, and images or analysis results are optionally visualized on a monitor or screen. In some embodiments, computer software comprises algorithms for identifying regions of images (slides, spots, etc.) of a sample, such as a gridding algorithm. Such systems are optionally automated, wherein images for alignment determination are acquired, optionally processed, and analyzed without external intervention. Other devices, systems, and methods for determining mask alignment are also consistent with the specification.

Further disclosed herein are arrays comprising the molecules disclosed herein. In some aspects, the arrays comprise a nucleoside, nucleotide, polynucleotide, peptide, peptoid, saccharide, aptamer, or antibody or fragment thereof chemically bound to the linker. In one aspect, the nucleoside, nucleotide, polynucleotide, peptide, peptoid, saccharide, aptamer, or antibody or fragment thereof comprise a chemical library. In some embodiments, the array is a peptide array. In some aspects, the peptide array is synthesized in situ.

Arrays of polymers can be synthesized using the methods and compositions described herein. For example, an array is synthesized using standard steps such as deprotection and coupling/extension, optionally with any number of additional steps, such as washing steps before, in between, or after synthesis steps. Polymers in some cases require different or additional steps such as oxidation, capping, cleavage, or other step. Additional polymers are also synthesized with the methods and compositions described herein. Often an alignment determination is made before or after one or more steps (or cycles) during array synthesis. For example one spot in a nearby inter-feature region is deprotected, and subjected to an alignment determination method described herein. Subsequent synthesis steps optionally also include an alignment determination method described herein. In some cases, this process is integrated until the desired polymer is synthesized. In some embodiments, the polymer is a peptide. In some instances, one or more spots are used to measure alignment only once. In some instances, spots are measured more than once to obtain averages for an alignment determination. In some embodiments, array synthesis comprises at least a first cycle and a second cycle, wherein a different spot is used for an alignment determination for the first cycle than for an alignment determination in the second cycle. Alternative timing and use of various combinations of spots for determining alignment are also consistent with the methods and compositions described herein.

Definitions

The terms "attach", "bind", "couple", and "link" are used interchangeably and refer to covalent interactions (e.g., by chemically coupling), or non-covalent interactions (e.g., ionic interactions, hydrophobic interactions, hydrogen bonds, or hybridization). The terms "specific", "specifically", or "specificity" refer to the preferential recognition, contact, and formation of a stable complex between a first molecule and a second molecule compared to that of the first molecule with any one of a plurality of other molecules (e.g., substantially less to no recognition, contact, or formation of a stable complex between the first molecule and any one of the plurality of other molecules). For example, two molecules may be specifically attached, specifically bound, specifically coupled, or specifically linked. Furthermore, "binding" may refer to either a specific interaction, such as the interaction of an antibody with an epitope, or it may refer to a non-specific interaction.

Nomenclature

Unless otherwise indicated, the term "alkyl" as employed herein alone or as part of another group can include both straight and branched chain hydrocarbons, containing, for instance, 1 to 20 carbons, 1 to 10 carbons, or 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups including 1 to 4 substituents such as halo, for example F, Br, Cl or I or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxyl, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl and/or alkylthio.

Unless otherwise indicated, the term "cycloalkyl" as employed herein alone or as part of another group can include saturated or partially unsaturated (containing 1 or 2 double bonds) cyclic hydrocarbon groups containing 1 to 3 rings, including monocyclic alkyl, bicyclic alkyl (or bicycloalkyl) and tricyclic alkyl (tricycloalkyl), containing a total of 3 to 20 carbons forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl and cyclododecyl, cyclohexenyl, adamantyl, and the like, any of which may be optionally substituted with 1 to 4 substituents such as halogen, alkyl, alkoxy, hydroxyl, aryl, aryloxy, arylalkyl, cycloalkyl, hyroxyalkyl, alkylamido, alkanoylamino, oxo, acyl, arylcarbonylamino, amino, nitro, cyano, thiol and/or alkylthio and/or any of the substituents for alkyl.

The term "alkanoyl" as used herein alone or as part of another group can refer to alkyl linked to a carbonyl group.

Unless otherwise indicated, the term "alkenyl" as used herein by itself or as part of another group can refer to straight or branched chain radicals of, for instance, 2 to 20 carbons in the normal chain, which include one to six double bonds in the normal chain, such as vinyl, 2-propenyl, 3-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4, 8, 12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxyl, heteroaryl, cycloheteroalkyl, alkanoylamino, alkylamido, arylcarbonyl-amino, nitro, cyano, thiol, alkylthio and/or any of the alkyl substituents set out herein.

Unless otherwise indicated, the term "alkynyl" as used herein by itself or as part of another group can refer to straight or branched chain radicals of 2 to 20 carbons in the normal chain, which include one triple bond in the normal chain, such as 2-propynyl, 3-butynyl, 2-butynyl, 4-pentynyl, 2-hexynyl, 3-hexynyl, 2-heptynyl, 3-heptynyl, 4-heptynyl, 3-octenyl, 3-nonenyl, 4-decenyl, 3-undecenyl, 4-dodecenyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxyl, alkanoylamino, alkylamido, arylcarbonylamino, nitro, cyano, thiol, and/or any of the alkyl substituents set out herein.

The term "halogen" or "halo" as used herein alone or as part of another group can refer to chlorine, bromine, fluorine, and iodine.

Unless otherwise indicated, the term "aryl" as employed herein alone or as part of another group can refer to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings) and may be optionally substituted through available carbon atoms with 1, 2, or 3 groups selected from hydrogen, halo, haloalkyl, alkyl, alkoxy, haloalkoxy, alkenyl, trifluoromethyl, trifluoromethoxy, alkynyl, cycloalkylalkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxyl, nitro, cyano, amino, substituted amino wherein the amino can include 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonyloxy, arylcarbonylamino, arylsulfinyl, arylsulfinylalkyl, arylsulfonylamino or arylsulfonaminocarbonyl and/or any of the alkyl substituents set out herein.

Unless otherwise indicated, the term "amino-substituted" as employed herein alone or as part of another group can refer to a chemical group having from 1 to 10 amino groups substituted thereon.

Unless otherwise indicated, the term "alkylthio" (also known as "thioalkyl") or "arylthio" (also known as "thioaryl") as employed herein alone or as part of another group can include any of the above alkyl or aryl groups linked to a sulfur atom.

Unless otherwise indicated, the term "selenoalkyl" as employed herein alone or as part of another group can include any of the above alkyl groups linked to a selenium atom.

Unless otherwise indicated, the term "alkylamino" or "arylamino" as employed herein alone or as part of another group can include any of the above alkyl or aryl groups linked to a nitrogen atom.

Unless otherwise indicated, the term "acyl" as employed herein by itself as part of another group, as defined herein, can refer to an organic radical linked to a carbonyl

group; examples of acyl groups include any of the R groups attached to a carbonyl, such as alkanoyl, alkenoyl, aroyl, aralkanoyl, heteroaroyl, cycloalkanoyl, cycloheteroalkanoyl and the like.

Unless otherwise indicated, the term "cycloheteroalkyl" as used herein alone or as part of another group can refer to a 5-, 6-, or 7-membered saturated or partially unsaturated ring which can include 1 to 2 heteroatoms such as nitrogen, oxygen and/or sulfur, linked through a carbon atom or a heteroatom, where possible, optionally via the linker $(CH_2)_r$ (where r is 1, 2, or 3).

Unless otherwise indicated, the term "heteroaryl" as used herein alone or as part of another group can refer to a 5- or 6-membered aromatic ring which can include 1, 2, 3 or 4 heteroatoms such as nitrogen, oxygen or sulfur, and such rings fused to an aryl, cycloalkyl, heteroaryl or cycloheteroalkyl ring, and includes possible N-oxides. The heteroaryl group may optionally include 1 to 4 substituents such as any of the substituents set out above for alkyl.

Unless otherwise indicated, the term "heteroalkyl" as used herein alone or as part of another group can refer to an alkyl group, as defined herein, which can include 1, 2, 3, or 4 heteroatoms such as nitrogen, oxygen or sulfur. The heteroalkyl group may optionally include 1 to 4 substituents such as any of the substituents set out above for alkyl.

All stereoisomers of compounds are contemplated, either in admixture or in pure or substantially pure form. Compounds can have asymmetric carbon centers at any of the carbon atoms including any one of the R substituents. Compounds can be either optically active or optically inactive. Asymmetric carbon centers can be independently in an R- or S-configuration. As defined herein asymmetric carbons are carbons that are a stereogenic center. Consequently, compounds of structures I, IA, IB, II, IIA, IIB, III, or IIIA can exist in enantiomeric or diastereomeric forms or in mixtures thereof. Enantiomeric mixtures can exist with an enantiomeric excess of 10%, 20%, 30%, 40%, 50%, 60%, 70%, 80%, 85%, 90%, 95%, 96%, 97%, 98%, 99%, 99.5% or 100%. Diastereomeric mixtures can exist with a diastereomeric ratio of 1:1, 2:1, 3:1, 4:1, 5:1, 6:1, 7:1, 8:1, 9:1, 10:1, 20:1, 50:1, 100:1, or 500:1. The processes for preparation of the molecules disclosed herein can utilize racemates, enantiomers or diastereomers as starting materials. When diastereomeric or enantiomeric products are prepared, they can be separated by conventional methods, for example, by chromatography or fractional crystallization.

A polynucleotide, as used herein, can be any type of nucleic acid molecule, including DNA, RNA, a hybridization thereof, or any combination thereof. For example, a polynucleotide can be cDNA, genomic DNA, mRNA, tRNA, rRNA, or microRNA.

A peptide, polypeptide, or protein can be contemplated to include any fragments thereof, in particular, immunologically detectable fragments. A peptide can be contemplated to include an α-peptide, a β-peptide, or a γ-peptide.

Methods

Methods disclosed herein include methods for deprotecting protected molecules. In some embodiments, protected molecules comprise a photoreactive protecting group. In some embodiments, protected molecules comprise an acid-sensitive protecting group.

The term "protecting group" refers to chemical moieties that block some or all reactive moieties and prevent such groups from participating in chemical reactions until the protective group is removed. A protecting group may also be referred to as a "protective group." It is preferred that each protective group be removable by a different means. Protective groups that are cleaved under totally disparate reaction conditions fulfill the requirement of differential removal. Protective groups can be removed by acid, base, hydrogenolysis, or photodeprotection. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. In some embodiments, groups such as trityl, dimethoxytrityl, Boc, and Fmoc groups are acid labile and may be use to protect nitrogen reactive moieties. In some embodiments, groups such as trityl and dimethoxytrityl may be used to protect sulfur reactive moieties. Removal of acid labile protecting groups may be accomplished with any method familiar to a skilled artisan. In some embodiments, an acid labile protecting group may be removed by bulk aqueous acid. In some embodiments, an acid labile protecting group may be removed by photoacids or photoacid generators. In some embodiments, photoacid generators may be ionic or non-ionic. In some embodiments, photoacid generators may utilize a sensitizer or be sensitizer-free. In some embodiments, photoacid generators may generate in situ such acids as tosylic acid, triflic acid, butanesulfonic acid, nitric acid. In some embodiments, photoacid generators may be used to remove acid-labile protecting groups at 20° C., 30° C., 40° C., 50° C., 60° C., 70° C., 80° C., 90° C., 100° C., 110° C., 120° C., 130° C., 140° C., 150° C., 160° C., 170° C., 180° C., 190° C., or 200° C. In some embodiments, photoacid generators may be used to remove acid-labile protecting groups at from 155° C.-175° C. In some embodiments photoacid generators may release acid upon stimulation with UV light having a wavelength from 193 nm-450 nm.

Also disclosed are methods for detecting chromophoric signals from arrays. In some embodiments, a chromophoric signal may be fluorescent or phosphorescent. In some embodiments, a chromophoric signal may emitted by a label or labeled probe.

A label refers to a molecule that, when attached to another molecule provides or enhances a means of detecting the other molecule. A signal emitted from a label can allow detection of the molecule or complex to which it is attached, and/or the label itself. For example, a label can be a molecular species that elicits a physical or chemical response that can be observed or detected by the naked eye or by means of instrumentation such as, without limitation, scintillation counters, colorimeters, UV spectrophotometers and the like. Labels include but are not limited to, radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. A fluorescence or fluorescent label or tag emits detectable light at a particular wavelength when excited at a different wavelength. A radiolabel or radioactive tag emits radioactive particles detectable with an instrument such as, without limitation, a scintillation counter. Other signal generation detection methods include: chemiluminescence detection, electrochemiluminescence detection, Raman energy detection, colorimetric detection, hybridization protection assays, and mass spectrometry. If the binding moiety is labeled, the methods of detection could include fluorescence, luminescence, radioactivity, and the like.

Methods disclosed herein can also include synthesizing coatings on solid supports. Characteristics of coatings prepared by the methods disclosed herein can be analyzed by various methods understood by a person of skill in the art. Methods of analysis can include, ellipsometry, water contact angle (WCA), X-ray photoelectron spectroscopy (XPS), atomic force microscopy (AFM), colorimetry, mass-spectrometry, including MALDI-MS, and the like.

In some embodiments, forming coatings can comprise coupling an aminosilane to a substrate. In some embodiments, the aminosilane can comprise 3-aminopropyltriethoxysilane (APTES), 3-aminopropylmethyldiethoxysilane (APDEMS), or 3-aminopropyldiisopropylethoxysilane (APDIPES).

In some embodiments, forming coatings can comprise a first step comprising forming a first coating layer. In some embodiments, the first step can comprise forming an oxygen-silicon bond between a sold substrate and a first molecule. In some embodiments, the first molecule can comprise a silicon at a first end and an epoxide, isocyanate, or thioisocyanate at a second end. In some embodiments, the first step can be performed in solution phase or in gas phase. In some embodiments, forming coatings can further comprise a second step comprising coupling a second molecule to the epoxide, isocyanate, or thioisocyanate of the first molecule to form a second coating layer. Coatings, as used herein, can be understood to encompass both single layer coatings and coatings comprising a first layer and a second layer. In some embodiments, the second molecule can have a boiling point of about 100° C., 110° C., 120° C., 130° C., 140° C., 150° C., 160° C., 170° C., 180° C., 190° C., 200° C., 210° C., 220° C., 230° C., 240° C., 250° C., 260° C., 270° C., 280° C., 290° C., 300° C., 310° C., 320° C., 330° C., 340° C., or 350° C. In some embodiments, the second step can comprise using a diluent. In some embodiments, a diluent can be an alcohol. In some embodiments, the alcohol can be ethanol, 1-propanol, 2-propanol (also known as isopropanol), 1-butanol, 2-butanol, tert-butanol, 1-pentanol, 2-pentanol, 3-pentanol, 3-methylbutan-1-ol (also known as isoamyl or isopentyl alcohol), 2-methylbutan-1-ol, 2,2-dimethylpropan-1-ol (also known as neopentyl alcohol), 3-methylbutan-2-ol, or 2-methylbutan-2-ol (also known as tert-amyl alcohol).

In some embodiments, formation of a coating can be accomplished by a deposition reaction. In some embodiments, the deposition reaction can be a chemical vapor deposition reaction. In some embodiments, coatings can be characterized by their water contact angle. In some embodiments, coatings can have a water contact angle of about 10°, 20°, 30°, 40°, 50°, 60°, 70°, 80°, 90°, 100°, 110°, 120°, 130°, 140°, 150°, or 160°. In some embodiments, coatings can have a contact angle from about 10° to about 120°. In some embodiments, coatings can have a water contact angle from about 40° to about 90°. In some embodiments, coatings can be characterized by their thickness. In some embodiments, thickness can be measured by ellipsometry. In some embodiments, coatings can have a thickness of about 0.5 angstroms (Å), 0.6 Å, 0.7 Å, 0.8 Å, 0.9 Å, 1 Å, 2 Å, 3 Å, 4 Å, 5 Å, 6 Å, 7 Å, 8 Å, 9 Å, 10 Å, 11 Å, 12 Å, 13 Å, 14 Å, 15 Å, 16 Å, 17 Å, 18 Å, 19 Å, 20 Å, 25 Å, 30 Å, 35 Å, 40 Å, 45 Å, 50 Å, 60 Å, 70 Å, 80 Å, 90 Å, or 100 Å. In some embodiments, coatings can have a thickness of from about 1 Å to about 10 Å. In some embodiments, coatings can have a thickness of from about 5 Å to about 7 Å. In some embodiments, coatings can be characterized by their smoothness. In some embodiments, coating smoothness can be measured by AFM. In some embodiments, coatings can have a smoothness of a root mean square of roughness ($R_q$) of about 0.10 nm, 0.11 nm, 0.12 nm, 0.13 nm, 0.14 nm, 0.15 nm, 0.16 nm, 0.17 nm, 0.18 nm, 0.19 nm, 0.20 nm, 0.21 nm, 0.22 nm, 0.23 nm, 0.24 nm, 0.25 nm, 0.26 nm, 0.27 nm, 0.28 nm, 0.29 nm, or 0.30 nm. In some embodiments, coatings can have an $R_q$ of from about 0.1 nm to about 0.3 nm. In some embodiments, coatings can have an Rq of from about 0.2 to about 0.25 nm. In some embodiments, coatings can have a density of amino groups of about $1\times10^9$, $1\times10^{10}$, $1\times10^{11}$, $1\times10^{12}$, $1\times10^{13}$, $1\times10^{14}$, or $1\times10^{15}$ amino groups per square centimeter.

In some embodiments, coatings can be coupled at the amine to a target analyte to form a target analyte-functionalized coating. In some embodiments, a target analyte can be a peptide. A peptide can be from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids. In some embodiments, peptides can comprise a library of peptides. In some embodiments, peptides can have protected side chains. In some embodiments, peptide side chains can be protected as benzyl ethers. In some embodiments, a coating can be coupled to a peptide by stepwise coupling of each of amino acid of the peptide.

Some embodiments comprise functionalizing an amino coating. Amino coatings can be functionalized by coupling the amino groups of the amino coating to molecules. A molecule can be a building block. In some embodiments, coupling comprises: coupling of an amino group to the carboxylic acid of a first building block. In some embodiments, a building block can comprise a carboxylic acid and a protected amine. In some embodiments, a building block can be an N-protected amino acid. In some embodiments, the protected amino acid can comprise a Boc-protected amine or an Fmoc-protected amine. In some embodiments, coupling can further comprise deprotection of the coupled building block. In some embodiments, coupling can further comprise coupling of the amino group of the deprotected first building block to the carboxylic acid of a second building block. In some embodiments, functionalizing of an amino coating can comprise iterative couplings to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 building blocks. In some embodiments, protected building blocks can be protected amino acids.

In some embodiments, functionalizing an amino coating can further comprise performing a capping step after any one of the described coupling steps. Capping can comprise reacting amino groups with a reagent to form a protected, or capped, amino group. Capping can comprise reacting amino groups that were not consumed in the preceding coupling reaction. Capping reagents can comprise acetic anhydride, acetyl chloride, acetyl fluoride, or an acylglycine. In some aspects, the capping step can form an alkylamine, arylamine, acetamide, carbamate, phthalimide, enamine, sulfonamide, or N-protected amino acid. In some aspects, the N-protected amino acid can be an N-acyl-protected amino acid. In some aspects, the protected amino acid can be acetyl glycine.

In some embodiments, forming coatings can comprise a first step comprising forming a first coating layer. In some embodiments, the first step can comprise forming an oxygen-silicon bond between a solid substrate and a first molecule. In some embodiments, the first molecule can comprise a silicon at a first end and an epoxide, isocyanate, or thioisocyanate at a second end. In some embodiments, the first step can be performed in solution phase or in gas phase. In some embodiments, forming coatings can further comprise a second step comprising forming a second coating layer. In some embodiments, forming said second coating layer can comprise a chemical vapor deposition reaction.

Supports/Substrates/Solid Phases

The present disclosure provides solid supports (also known as solid phases, substrates, or supports). The nature and geometry of a support or substrate can depend upon a variety of factors, including the type of array (e.g., one-dimensional, two-dimensional or three-dimensional). Generally, a substrate can be composed of any material which will permit coupling of a nucleoside, nucleotide, polynucleotide, peptide, peptoid, saccharide, aptamer, or antibody or fragment thereof, which will not melt or degrade under the conditions used to couple said nucleoside, nucleotide, polynucleotide, peptide, peptoid, saccharide, aptamer, or antibody or fragment thereof to said solid support. A solid support can be composed of any material which will permit coupling of a target analyte, and/or other moiety at one or more discrete regions and/or discrete locations within the discrete regions. A solid support can be composed of any material which will permit washing or physical or chemical manipulation without dislodging a target analyte or binding moiety from the solid support.

A substrate may take a variety of configurations ranging from simple to complex, depending on the intended use of the array. Thus, a substrate can have an overall slide or plate configuration, such as a rectangular or disc configuration. A standard microplate configuration can be used. In some embodiments, the surface may be smooth or substantially planar, or have irregularities, such as depressions or elevations. For example, the substrates of the presently disclosed subject matter can include at least one surface on which a pattern of recombinant virion microspots can be coupled or deposited. In some instances, a substrate may have a rectangular cross-sectional shape, having a length of from about 10-200 mm, 40-150 mm, or 75-125 mm; a width of from about 10-200 mm, 20-120 mm, or 25-80 mm, and a thickness of from about 0.01-5.0 mm, 0.1-2 mm, or 0.2 to 1 mm.

A support may be organic or inorganic; may be metal (e.g., copper or silver) or non-metal; may be a polymer or nonpolymer; may be conducting, semiconducting or nonconducting (insulating); may be reflecting or nonreflecting; and may be porous or nonporous. A solid support as described above can be formed of any suitable material, including metals, metal oxides, semiconductors, polymers (particularly organic polymers in any suitable form including woven, nonwoven, molded, extruded, or cast), silicon, silicon oxide, and composites thereof.

Suitable materials for use as substrates include, but are not limited to, polycarbonate, gold, silicon, silicon oxide, silicon oxynitride, indium, tantalum oxide, niobium oxide, titanium, titanium oxide, platinum, iridium, indium tin oxide, diamond or diamond-like film, acrylic, styrene-methyl methacrylate copolymers, ethylene/acrylic acid, acrylonitrile-butadiene-styrene (ABS), ABS/polycarbonate, ABS/polysulfone, ABS/polyvinyl chloride, ethylene propylene, ethylene vinyl acetate (EVA), nitrocellulose, nylons (including nylon 6, nylon 6/6, nylon 6/6-6, nylon 6/9, nylon 6/10, nylon 6/12, nylon 11 and nylon 12), polyacrylonitrile (PAN), polyacrylate, polycarbonate, polybutylene terephthalate (PBT), poly(ethylene) (PE) (including low density, linear low density, high density, cross-linked and ultra-high molecular weight grades), poly(propylene) (PP), cis and trans isomers of poly(butadiene) (PB), cis and trans isomers of poly(isoprene), polyethylene terephthalate (PET), polypropylene homopolymer, polypropylene copolymers, polystyrene (PS) (including general purpose and high impact grades), polycarbonate (PC), poly(epsilon-caprolactone)

(PECL or PCL), poly(methyl methacrylate) (PMMA) and its homologs, poly(methyl acrylate) and its homologs, poly (lactic acid) (PLA), poly(glycolic acid), polyorthoesters, poly(anhydrides), nylon, polyimides, polydimethylsiloxane (PDMS), polybutadiene (PB), polyvinylalcohol (PVA), polyacrylamide and its homologs such as poly(N-isopropyl acrylamide), fluorinated polyacrylate (PFOA), poly(ethylene-butylene) (PEB), poly(styrene-acrylonitrile) (SAN), polytetrafluoroethylene (PTFE) and its derivatives, polyolefin plastomers, fluorinated ethylene-propylene (FEP), ethylene-tetrafluoroethylene (ETFE), perfluoroalkoxyethylene (PFA), polyvinyl fluoride (PVF), polyvinylidene fluoride (PVDF), polychlorotrifluoroethylene (PCTFE), polyethylene-chlorotrifluoroethylene (ECTFE), styrene maleic anhydride (SMA), metal oxides, glass, silicon oxide or other inorganic or semiconductor material (e.g., silicon nitride), compound semiconductors (e.g., gallium arsenide, and indium gallium arsenide), and combinations thereof.

Examples of well-known solid supports include polypropylene, polystyrene, polyethylene, dextran, nylon, amylases, glass, natural and modified celluloses (e.g., nitrocellulose), polyacrylamides, agaroses and magnetite. In some instances, the solid support can be silica or glass because of its great chemical resistance against solvents, its mechanical stability, its low intrinsic fluorescence properties, and its flexibility of being readily functionalized. In one embodiment, the substrate can be glass, particularly glass coated with nitrocellulose, more particularly a nitrocellulose-coated slide (e.g., FAST slides).

In some embodiments, the support can be planar. In some instances, the support can be spherical. In some instances, the support can be a bead. In some instances, a support can be magnetic. In some instances, a magnetic solid support can comprise magnetite, maghemitite, FePt, SrFe, iron, cobalt, nickel, chromium dioxide, ferrites, or mixtures thereof. In some instances, a support can be nonmagnetic. In some embodiments, the nonmagnetic solid support can comprise a polymer, metal, glass, alloy, mineral, or mixture thereof. In some instances a nonmagnetic material can be a coating around a magnetic solid support. In some instances, a magnetic material may be distributed in the continuous phase of a magnetic material. In some embodiments, the solid support comprises magnetic and nonmagnetic materials. In some instances, a solid support can comprise a combination of a magnetic material and a nonmagnetic material. In some embodiments, the magnetic material is at least about 5, 10, 20, 30, 40, 50, 60, 70, or about 80% by weight of the total composition of the solid support. In some embodiments, the bead size can be quite large, on the order of 100-900 microns or in some cases even up to a diameter of 3 mm. In other embodiments, the bead size can be on the order of 1-150 microns. The average particle diameters of beads can be in the range of about 2 μm to several millimeters, e.g., diameters in ranges having lower limits of 2 μm, 4 μm, 6 μm, 8 μm, 10 μm, 20 μm, 30 μm, 40 μm, 50 μm, 60 μm, 70 μm, 80 μm, 90 μm, 100 μm, 150 μm, 200 μm, 300 μm, or 500 μm, and upper limits of 20 μm, 30 μm, 40 μm, 50 μm, 60 μm, 70 μm, 80 μm, 90 μm, 100 μm, 150 μm, 200 μm, 300 μm, 500 μm, 750 μm, 1 mm, 2 mm, or 3 mm.

In some embodiments, the support can comprise an array. In some embodiments, the array comprises a target analyte. In some embodiments, the target analyte comprises a nucleoside, a nucleotide, a polynucleotide, a peptide, a peptoid, a saccharide, a polysaccharide, an aptamer, or an antibody or fragment thereof. In some embodiments, the target analyte comprises a library of target analytes.

In some embodiments, an array comprises a library of molecules. In some embodiments, the array can comprise at least about 100, 1000, 10,000, 100,000, $10^6$, $10^7$, $10^8$, $10^9$, $10^{10}$, $10^{11}$, $10^{12}$, $10^{13}$, $10^{14}$, or $10^{15}$ molecules per 1 cm². In some embodiments, a molecule can comprise a sequence of monomers. In some embodiments, the sequence of monomers can comprise a sequence of amino acids. In some embodiments, a feature can be a region on a substrate from about 0.5 microns to about 200 microns in diameter. In some embodiments, the array can have a plurality of features. In some embodiments, the center-to-center distance between features can be from about 1 micron to about 300 microns. In some embodiments, the array can comprise at least about 1,000, 10,000, 100,000, 200,000, 300,000, 400,000, or 500,000, 1 million, 2 million, 3 million, 4 million, or 8 million features per 1 cm². In some embodiments, at least about 40% of the molecules in the library are distinct. In some embodiments, at least about 50% of the molecules in the library are distinct. In some embodiments, at least about 60% of the molecules in the library are distinct. In some embodiments, at least about 70% of the molecules in the library are distinct. In some embodiments, at least about 80% of the molecules in the library are distinct. In some embodiments, at least about 90% of the molecules in the library are distinct. In some embodiments, at least 50% of the molecules in the library are at least 3, 4, 5, 6, 7, 8, 9, 10, 11, 12, 13, 14, 15, 16, 17, 18, 19, 20, 30, 40, 50, 60, 70, 80, 90, or 100 monomers in length. In some embodiments, at least 50% of the molecules in the library are at most 3, 4, 5, 6, 7, 8, 9, 10, 11, 12, 13, 14, 15, 16, 17, 18, 19, 20, 30, 40, 50, 60, 70, 80, 90, or 100 monomers in length. In some embodiments, the library comprises a median monomer length of about 3, 4, 5, 6, 7, 8, 9, 10, 11, 12, 13, 14, 15, 16, 17, 18, 19, 20, 30, 40, 50, 60, 70, 80, 90, or 100 monomers. In some embodiments, the array can comprise at least 10,000, 50,000, 100,000, 200,000, 300,000, 400,000, 500,000, 600,000, 700,000, 800,000, 900,000, $10^6$, or $10^7$ sequentially distinct library molecules. In some embodiments, the array substrate can be selected from wafers, slides, and beads. In some embodiments, the library can be an in-situ synthesized chemical library. In some embodiments, the molecules can be polynucleotides, peptides, peptoids, or polysaccharides.

Binding Moiety

An analyte binding moiety, also referred to as a binding moiety (or domain) can be the region, molecule, domain, portion, fragment, or moiety that binds to a target analyte. Thus, a binding moiety confers the ability to bind or specifically bind to given target. A binding moiety can be a nucleic acid molecule or can be proteinaceous. Binding moieties include, but are not limited to, RNAs DNAs, RNA-DNA hybrids, small molecules (e.g., drugs or metabolites), aptamers, polypeptides, proteins, antibodies, viruses, virus particles, cells, fragments thereof, and combinations thereof.

In some embodiments, a binding moiety can be a polypeptide, a protein, or any fragment thereof. In some embodiments, a polypeptide or protein can be an engineered or recombinant polypeptide or protein. In some embodiments, a binding moiety is an antibody or fragment thereof. An antibody can be of any isotype (e.g., IgG, IgE, IgM, IgD, IgA and IgY), class ($IgG_1$, $IgG_2$, $IgG_3$, $IgG_4$, $IgA_1$, $IgA_2$), subclass or modified version thereof. Antibodies may include complete immunoglobulins or fragments thereof. An antibody fragment can refer to one or more fragments of an antibody that retains the ability to specifically bind to a target molecule, such as an antigen.

In some embodiments, a binding moiety can be an aptamer. An aptamer is an isolated nucleic acid molecule that can bind with high specificity and affinity to a target analyte, such as a protein. An aptamer comprises a three dimensional structure held in certain conformation(s) that provide chemical contacts to specifically bind a given target. In some embodiments, a binding moiety is small molecule. For example, a small molecule can be a macrocyclic molecule, an inhibitor, a drug, or chemical compound. In some embodiments, a binding moiety is a cell. For example, a binding moiety can be an intact cell, a cell treated with a compound (e.g. a drug), a fixed cell, a lysed cell, or any combination thereof.

Detection Methods

Detection methods for detecting bound binding moieties and labeled probes can include photometric and non-photometric means. In some embodiments, such methods include a method to detect and measure absorbance, fluorescence, refractive index, polarization or light scattering. These include direct and/or indirect means to measure such parameters. Methods involving fluorescence include fluorescent tagging in immunological methods such as ELISA or sandwich assay. Methods involving refractive index include surface Plasmon resonance (SPR), grating coupled methods (e.g., sensors uniform grating couplers, wavelength-interrogated optical sensors (WIOS) and chirped grating couplers), resonant minor and interferometric techniques. Methods involving polarization include ellipsometry. Light scattering methods may also be used. Other means for tagging and/or separating and/or detecting can also include magnetic means. Magnetic resonance imaging (MRI), or gas phase ion spectrometry may all be used.

Non-photometric methods of detection include, without limitation, magnetic resonance imaging, gas phase ion spectrometry, atomic force microscopy and multipolar coupled resonance spectroscopy. Magnetic resonance imaging (MRI) is based on the principles of nuclear magnetic resonance (NMR), a spectroscopic technique used by scientists to obtain microscopic chemical and physical information about molecules. Gas phase ion spectrometers include mass spectrometers, ion mobility spectrometers and total ion current measuring devices.

Binding assays can also be useful, e.g., for identifying disease related antibodies (binding moieties) that interact with the target analytes described herein. For example, antibodies or other molecules that bind target analytes can be identified in binding assays. Binding assays can involve, but are not limited to, use of isolated polypeptides, crude extracts, or cell-based assays. In some embodiments the assays described herein can be used to a) identify subjects whose have a first disease or a second disease; (b) assess the impact of an disease therapy; and (c) monitor disease progression.

Binding assays can involve contacting a target analyte with a sample comprising a binding moiety (antibody) and allowing sufficient time for the molecule and test agents to form a binding complex. Any binding complexes formed can be detected using any of a number of established analytical techniques. Binding assays include, but are not limited to, methods that measure co-precipitation or co-migration on non-denaturing SDS-polyacrylamide gels, co-migration on Western blots, enzyme linked immunosorbent assay (ELISA), radioimmunoassay (RIA), immunoradiometric assay, fluoroimmunoassay, chemiluminescent assay, bioluminescent assay, fluorescence activated cells sorting (FACS), or fluorescence resonance energy transfer (FRET).

Diagnostics

The methods and apparatus disclosed herein can be used to screen for various diseases or conditions, including an alteration in the state of the body or of some of the organs, interrupting or disturbing the performance of the functions and/or causing symptoms such as discomfort, dysfunction, distress, or even death to the person afflicted or those in contact with the person. A disease or condition can also include distemper, ailing, ailment, malady, disorder, sickness, illness, complain, interdisposition and/or affectation.

For example, samples containing binding moieties from a diseased animal can be simultaneously screened for the binding moieties' ability to interact with an array. These interactions can be compared to those of samples from individuals that are not in a disease state, not presenting symptoms of persons in the disease state, or presenting symptoms of the disease state. For example, the levels of binding moieties in samples from a diseased animal can be simultaneously determined. These levels can be compared to those of samples from individuals that are not in a disease state, not presenting symptoms of persons in the disease state, or presenting symptoms of the disease state.

The methods, kits, and compositions described herein can be used in medical diagnostics, drug discovery, molecular biology, immunology and toxicology. Arrays can be used for large scale binding assays in numerous diagnostic and screening applications. The multiplexed measurement of quantitative variation in levels of large numbers of target analytes (e.g., proteins) allows the recognition of patterns defined by several to many different target analytes. The multiplexed identification of large numbers of interactions between target analytes and binding moieties allows for the recognition of binding and interaction patterns defined by several to many different interactions between target analytes and binding moieties. Many physiological parameters and disease-specific patterns can be simultaneously assessed. One embodiment involves the separation, identification and characterization of proteins present in a biological sample. For example, by comparison of disease and control samples, it is possible to identify disease specific target analytes. These target analytes can be used as targets for drug development or as molecular markers of disease. Substrate-bound molecules of the present invention may also be used as solid phase filtration devices, wherein capture agents are attached to the surface.

In some embodiments, methods can be methods for diagnosing or detecting a disease or condition such as a cancer, inflammatory disease, immune disease, autoimmune disease, cardiovascular disease, neurological disease, infectious disease, metabolic disease, or a perinatal condition. For example, the disease or condition can be a tumor, neoplasm, or cancer. The cancer can be, but is not limited to, breast cancer, ovarian cancer, lung cancer, colon cancer, hyperplastic polyp, adenoma, colorectal cancer, high grade dysplasia, low grade dysplasia, prostatic hyperplasia, prostate cancer, melanoma, pancreatic cancer, brain cancer (such as a glioblastoma), hematological malignancy, hepatocellular carcinoma, cervical cancer, endometrial cancer, head and neck cancer, esophageal cancer, gastrointestinal stromal tumor (GIST), renal cell carcinoma (RCC) or gastric cancer. The colorectal cancer can be CRC Dukes B or Dukes C-D. The hematological malignancy can be B-Cell Chronic Lymphocytic Leukemia, B-Cell Lymphoma-DLBCL, B-Cell Lymphoma-DLBCL-germinal center-like, B-Cell Lymphoma-DLBCL-activated B-cell-like, or Burkitt's lymphoma. The disease or condition can also be a premalignant condition, such as Barrett's Esophagus. The disease or condition can also be an inflammatory disease, immune disease, or autoimmune disease. For example, the disease may be inflammatory bowel disease (IBD), Crohn's disease (CD), ulcerative colitis (UC), pelvic inflammation, vasculitis, psoriasis, diabetes, autoimmune hepatitis, Multiple Sclerosis, Myasthenia Gravis, Type I diabetes, Rheumatoid Arthritis, Psoriasis, Systemic Lupus Erythematosis (SLE), Hashimoto's Thyroiditis, Grave's disease, Ankylosing Spondylitis Sjogrens Disease, CREST syndrome, Scleroderma, Rheumatic Disease, organ rejection, Primary Sclerosing Cholangitis, or sepsis. The disease or condition can also be a cardiovascular disease, such as atherosclerosis, congestive heart failure, vulnerable plaque, stroke, or ischemia. The cardiovascular disease or condition can be high blood pressure, stenosis, vessel occlusion or a thrombotic event. The disease or condition can also be a neurological disease, such as Multiple Sclerosis (MS), Parkinson's Disease (PD), Alzheimer's Disease (AD), schizophrenia, bipolar disorder, depression, autism, Prion Disease, Pick's disease, dementia, Huntington disease (HD), Down's syndrome, cerebrovascular disease, Rasmussen's encephalitis, viral meningitis, neuropsychiatric systemic lupus erythematosus (NPSLE), amyotrophic lateral sclerosis, Creutzfeldt-Jacob disease, Gerstmann-Straussler-Scheinker disease, transmissible spongiform encephalopathy, ischemic reperfusion damage (e.g., stroke), brain trauma, microbial infection, or chronic fatigue syndrome. The condition may also be fibromyalgia, chronic neuropathic pain, or peripheral neuropathic pain. The disease or condition may also be an infectious disease, such as a bacterial, viral or yeast infection. For example, the disease or condition may be Whipple's Disease, Prion Disease, cirrhosis, methicillin-resistant *Staphylococcus aureus*, HIV, hepatitis, syphilis, meningitis, malaria, tuberculosis, or influenza. The disease or condition can also be a perinatal or pregnancy related condition (e.g., preeclampsia or preterm birth), zika virus, dengue fever, flavivirus, or a metabolic disease or condition, such as a metabolic disease or condition associated with iron metabolism.

In some embodiments, methods are methods for diagnosing or detecting an autoimmune disorder. In some embodiments, methods can be methods for determining a disease or condition or he progression of a disease or condition. Non-limiting examples of disorder associated with the immune system can include: autoimmune disorders, inflammatory diseases, HIV, rheumatoid arthritis, diabetes mellitus type 1, systemic lupus erythematosus, scleroderma, multiple sclerosis, severe combined immunodeficiency (SCID), DiGeorge syndrome, ataxia-telangiectasia, seasonal allergies, perennial allergies, food allergies, anaphylaxis, mastocytosis, allergic rhinitis, atopic dermatitis, Parkinson's, Alzheimer's, hypersplenism, leukocyte adhesion deficiency, X-linked lymphoproliferative disease, X-linked agammaglobulinemia, selective immunoglobulin A deficiency, hyper IgM syndrome, autoimmune lymphoproliferative syndrome, Wiskott-Aldrich syndrome, chronic granulomatous disease, common variable immunodeficiency (CVID), hyperimmunoglobulin E syndrome, Hashimoto's thyroiditis.

Kits

Also provided are kits that find use in practicing the subject methods, as mentioned above. A kit can include one or more of the compositions described herein. A kit can include at least one nucleoside, nucleotide, polynucleotide, peptide, peptoid, saccharide, aptamer, or antibody or fragment thereof. A kit can include at least one binding moiety.

A kit can include a solid support. In some embodiments, the solid support is already functionalized with at least one molecule of structure I. In some embodiments, the solid support is already functionalized with at least one nucleoside, nucleotide, polynucleotide, peptide, peptoid, saccharide, aptamer, or antibody or fragment thereof. A kit can include a reagent for coupling at least one nucleoside, nucleotide, polynucleotide, peptide, peptoid, saccharide, aptamer, or antibody or fragment thereof to the solid support.

The kit components may be present in separate containers, or one or more of the components may be present in the same container, where the containers may be storage containers and/or containers that are employed during the assay for which the kit is designed.

In addition to the above components, the subject kits may further include instructions for practicing the subject methods. These instructions may be present in the subject kits in a variety of forms, such as printed information on a suitable medium or substrate (e.g., a piece or pieces of paper on which the information is printed), in the packaging of the kit, or in a package insert. Yet another means would be a computer readable medium (e.g., diskette or CD), on which the information has been recorded. Yet another means that may be present is a website address which may be used via the internet to access the information at a removed site.

Communicating a Result

Additional embodiments relate to the communication of assay results or diagnoses or both to technicians, physicians or subjects, for example. In certain embodiments, computers will be used to communicate results of the assessing or diagnoses or both to interested parties, e.g., physicians and their subjects. In some embodiments, the assessing can be performed or results analyzed in a country or jurisdiction which differs from the country or jurisdiction to which the results or diagnoses are communicated. In some embodiments, a diagnosis based on the presence or absence in a test subject of a binding moiety or a binding signature, or signal identified may be communicated to the subject as soon as possible after the diagnosis is obtained. The diagnosis may be communicated to the subject by the subject's treating physician. Alternatively, the diagnosis may be sent to a test subject by email or communicated to the subject by phone. A computer may be used to communicate the diagnosis by email or phone. In certain embodiments, the message containing results of a diagnostic test may be generated and delivered automatically to the subject using a combination of computer hardware and software which will be familiar to artisans skilled in telecommunications. In certain embodiments, all or some of the method steps, including the assaying of samples, diagnosing of diseases, and communicating of method results or diagnoses, may be carried out in diverse (e.g., foreign) jurisdictions.

Embodiments

Described herein are methods comprising: deprotecting a subset of a plurality of protected molecules comprising a photoreactive or acid-sensitive protecting group to form a plurality of deprotected molecules; wherein the plurality of protected molecules are comprised in a first array region; wherein the plurality of deprotected molecules are comprised in a second array region; and wherein the distance from a boundary of the first array region to a boundary of the second array region is substantially uniform; and detecting alignment of the second array region with the first array region, wherein the detecting alignment comprises detecting a chromophoric signal from at least one of the first array region and the second array region; and wherein the first array region and the second array region are substantially located in a space between two or more peptide features. In some embodiments, the chromophoric signal is a fluorescent signal or a phosphorescent signal. In some embodiments, the first array region and the second array region have substantially the same shape. In some embodiments, the distance from the boundary of the first array region to the boundary of the second array region is non-zero. In some embodiments, the deprotecting a subset of a plurality of protected molecules comprises a photolithographic mask. In some embodiments, each of molecules of the plurality of protected molecules independently has the structure:

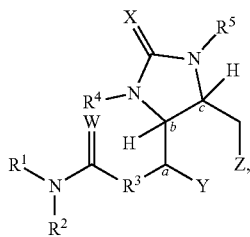

or a salt thereof,
wherein W is S or O;
X is S, O, or NH;
Y and Z are H, or wherein Y and Z are combined to form a S, O, or methylene;
$R^1$ is alkyl, alkenyl, alkynyl, aryl, heteroalkyl, heteroalkenyl, or heteroaryl; and wherein $R^1$ further comprises a solid support;
$R^2$ is hydrogen or alkyl;
$R^3$ is alkyl, alkenyl, aryl, heteroalkyl, heteroalkenyl, heteroaryl, or arylalkyl;
$R^4$ and $R^5$ are independently hydrogen, alkyl, alkenyl, aryl, heteroalkyl, heteroalkenyl, heteroaryl, or arylalkyl; wherein at least one of $R^4$ and $R^5$ is not hydrogen; and
(a) is a first carbon center, wherein the first carbon center is in an R-configuration, an S-configuration, or is a non-stereogenic center;
(b) is a second carbon center, wherein the second carbon center is in the R-configuration or the S-configuration; and
(c) is a third carbon center, wherein the third carbon center is in the R-configuration or the S-configuration.

In some embodiments, the deprotecting of the subset of protected molecules forms the plurality of deprotected molecules, such that each of the molecules of the plurality of deprotected thereof independently has the structure:

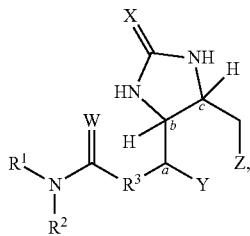

or a salt thereof, wherein W is S or O;
X is S, O, or NH;
Y and Z are H, or wherein Y and Z are combined to form a S, O, or methylene;
$R^1$ is alkyl, alkenyl, alkynyl, aryl, heteroalkyl, heteroalkenyl, or heteroaryl; and wherein $R^1$ further comprises a solid support;
$R^2$ is hydrogen or alkyl;
$R^3$ is alkyl, alkenyl, aryl, heteroalkyl, heteroalkenyl, heteroaryl, or arylalkyl;
(a) is a first carbon center, wherein the first carbon center is in an R-configuration, an S-configuration, or is a non-stereogenic center;
(b) is a second carbon center, wherein the second carbon center is in the R-configuration or the S-configuration; and
(c) is a third carbon center, wherein the third carbon center is in the R-configuration or the S-configuration.

In some embodiments, each of molecules of the plurality of protected molecules thereof independently has the structure:

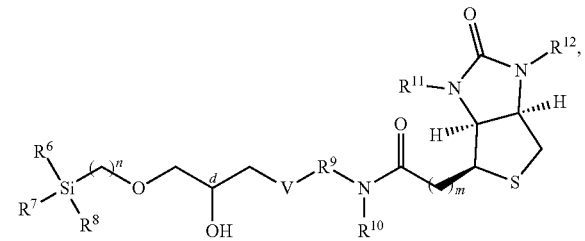

or a salt thereof,
wherein V is NH, O, S, or Se;
n=1-6, m=1-6;
$R^6$, $R^7$, and $R^8$ are the same or different and are independently hydrogen, alkyl, alkoxy, silyl, or siloxy, wherein at least one of $R^6$, $R^7$, and $R^8$ further comprises a solid phase;
$R^9$ is alkyl, alkenyl, alkynyl or aryl, all optionally substituted with at least one of halo, alkyl, polyhaloalkyl, alkyoxy, haloalkoxy, polyhaloalkoxy, alkoxycarbonyl, alkenyl, alkynyl, cycloalkyl, cycloalkylalkyl, hydroxyl, hydroxyalkyl, nitro, cyano, amino, substituted amino, alkylamino, dialkylamino, thiol, alkylthio, alkylcarbonyl, acyl, alkoxycarbonyl, aminocarbonyl, alkylsulfinyl, sulfonamide, or sulfonyl;
$R^{10}$ is hydrogen or alkyl;
$R^{11}$ and $R^{12}$ are independently hydrogen or arylalkyl; wherein at least one of $R^{11}$ and $R^{12}$ is not hydrogen; and
(d) is a carbon center, wherein the carbon center is in the R-configuration or the S-configuration.

In some embodiments, each of molecules of the plurality of protected molecules independently has the structure:

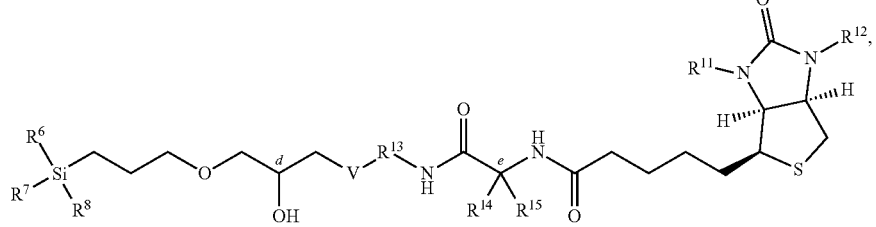

or a salt thereof, wherein V is NH, O, S, or Se;

R$^6$, R$^7$, and R$^8$ are the same or different and are independently hydrogen, alkyl, alkoxy, silyl, or siloxy, wherein at least one of R$^6$, R$^7$, and R$^8$ further comprises a solid phase;

R$^{13}$ is alkyl, heteroalkyl, amino-substituted alkyl, amino-substituted heteroalkyl, amidoalkyl, amidoheteroalkyl, amino-substituted amidoheteroalkyl, each optionally substituted with at least one of alkyl, heteroalkyl, amino-substituted alkyl, amino-substituted heteroalkyl, amidoalkyl, amidoheteroalkyl, or amino-substituted amidoheteroalkyl;

R$^{14}$ and R$^{15}$ are the same or different and are independently hydrogen, halo, alkyl, alkenyl, aryl, heteroalkyl, arylalkyl, hydroxyarylalkyl, heteroarylalkyl, cycloalkyl, thioalkyl, selenoalkyl, hydroxyalkyl, or amino-substituted alkyl;

R$^{11}$ and R$^{12}$ are independently hydrogen or arylalkyl, wherein at least one of R$^4$ and R$^5$ is not hydrogen;

(d) is a first carbon center, wherein the first carbon center is in the R-configuration or the S-configuration; and (e) is a second carbon center, wherein the second carbon center is in the R-configuration, the S-configuration, or is a non-stereogenic center.

In some embodiments, R$^{11}$ is hydrogen and R$^{12}$ is trityl, methoxytrityl, or dimethoxytrityl. In some embodiments, R$^{13}$ is ethylenediamino, (ethylenedioxy)bis(ethylamino), tris(2-aminoethyl)amino, polyamidoamino, or polyallylamino. In some embodiments, R$^{14}$ and R$^{15}$ are hydrogen. In some embodiments, R$^{14}$ is hydrogen and R$^{15}$ is hydroxymethyl. In some embodiments, deprotecting comprises a photodeprotection reaction. In some embodiments, the photodeprotection reaction comprises a photoacid or photoacid generator. In some embodiments, detecting alignment comprises binding a detectably labeled probe to the plurality of deprotected molecules. In some embodiments, the detectably labeled probe comprises a chromophoric dye. In some embodiments, the labeled polypeptide comprises streptavidin, neutravidin, or captavidin, or a salt of any of the above. In some embodiments, the labeled polypeptide or salt thereof is a labeled with a chromophoric dye. In some embodiments, the chromophoric dye is a fluorescent dye or a phosphorescent dye. In some embodiments, each of molecules of the plurality of protected molecules independently has the structure:

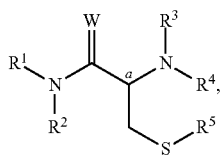

or a salt thereof, wherein W is S or O;

R$^1$ is alkyl, alkenyl, alkynyl, aryl, heteroalkyl, heteroalkenyl, or heteroaryl; and wherein R$^1$ further comprises a solid support;

R$^2$, R$^3$, and R$^4$ are independently hydrogen or alkyl;

R$^5$ is alkyl, alkenyl, aryl, heteroalkyl, heteroalkenyl, heteroaryl, or arylalkyl; and wherein (a) is a carbon center, wherein the carbon center is in an R-configuration or an S-configuration.

In some embodiments, the deprotecting of the subset of protected molecules forms the plurality of deprotected molecules, such that each of the molecules of the plurality of deprotected molecules independently has the structure:

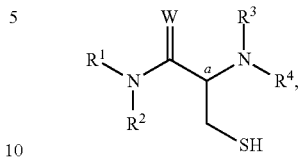

or a salt thereof, wherein W is S or O;

R$^1$ is alkyl, alkenyl, alkynyl, aryl, heteroalkyl, heteroalkenyl, or heteroaryl; and wherein R$^1$ further comprises a solid support;

R$^2$, R$^3$, and R$^4$ are independently hydrogen or alkyl; and wherein (a) is a carbon center, wherein the carbon center is in an R-configuration or an S-configuration.

In some embodiments, each of molecules of the plurality of protected independently has the structure:

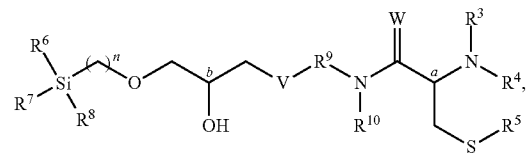

or a salt thereof, wherein V is NH, O, S, or Se;

n=1-6;

R$^3$ and R$^4$ are independently hydrogen or alkyl;

R$^5$ is alkyl, alkenyl, aryl, heteroalkyl, heteroalkenyl, heteroaryl, or arylalkyl;

R$^6$, R$^7$, and R$^8$ are the same or different and are independently hydrogen, alkyl, alkoxy, silyl, or siloxy, wherein at least one of R$^6$, R$^7$, and R$^8$ further comprises a solid phase;

R$^9$ is alkyl, alkenyl, alkynyl or aryl, all optionally substituted with at least one of halo, alkyl, polyhaloalkyl, alkyoxy, haloalkoxy, polyhaloalkoxy, alkoxycarbonyl, alkenyl, alkynyl, cycloalkyl, cycloalkylalkyl, hydroxyl, hydroxyalkyl, nitro, cyano, amino, substituted amino, alkylamino, dialkylamino, thiol, alkylthio, alkylcarbonyl, acyl, alkoxycarbonyl, aminocarbonyl, alkylsulfinyl, sulfonamide, or sulfonyl;

R$^{10}$ is hydrogen or alkyl; and (a) is a first carbon center, wherein the first carbon center is in an R-configuration or an S-configuration; and (b) is a second carbon center, wherein the second carbon center is in the R-configuration or the S-configuration.

In some embodiments, each of molecules of the plurality of protected molecules independently has the structure:

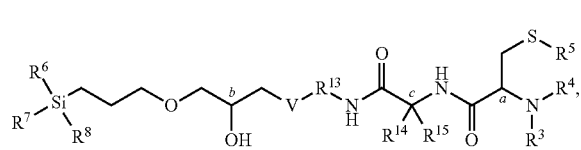

or a salt thereof, wherein V is NH, O, S, or Se;

$R^3$ and $R^4$ are independently hydrogen or alkyl;

$R^5$ is hydrogen or arylalkyl;

$R^6$, $R^7$, and $R^8$ are the same or different and are independently hydrogen, alkyl, alkoxy, silyl, or siloxy, wherein at least one of $R^6$, $R^7$, and $R^8$ further comprises a solid phase;

$R^{13}$ is alkyl, heteroalkyl, amino-substituted alkyl, amino-substituted heteroalkyl, amidoalkyl, amidoheteroalkyl, amino-substituted amidoheteroalkyl, each optionally substituted with at least one of alkyl, heteroalkyl, amino-substituted alkyl, amino-substituted heteroalkyl, amidoalkyl, amidoheteroalkyl, or amino-substituted amidoheteroalkyl, $R^{14}$ and $R^{15}$ are the same or different and are independently hydrogen, halo, alkyl, alkenyl, aryl, heteroalkyl, arylalkyl, hydroxyarylalkyl, heteroarylalkyl, cycloalkyl, thioalkyl, selenoalkyl, hydroxyalkyl, or amino-substituted alkyl;

(a) is a carbon center, wherein the carbon center is in the R-configuration or the S-configuration;

(b) is a second carbon center, wherein the second carbon center is in the R-configuration or the S-configuration; and (c) is a third carbon center, wherein the third carbon center is in the R-configuration, the S-configuration, or is a non-stereogenic center.

In some embodiments, $R^5$ is trityl, methoxytrityl, or dimethoxytrityl. In some embodiments, $R^{13}$ is ethylenediamino, (ethylenedioxy)bis(ethylamino), tris (2-aminoethyl)amino, polyamidoamino, or polyallylamino. In some embodiments, $R^{14}$ and $R^{15}$ are hydrogen. In some embodiments, deprotecting comprises a photodeprotection reaction. In some embodiments, the photodeprotection reaction comprises a photoacid or photoacid generator. In some embodiments, a deprotected molecule or salt thereof of the plurality of deprotected molecules or salts thereof comprises a sulfide, and wherein the method further comprises coupling the sulfide to a detectably labeled probe. In some embodiments, the detectably labeled probe comprises a chromophoric dye. In some embodiments, the chromophoric dye is a fluorescent dye. In some embodiments, the fluorescent dye is a maleimide dye. In some embodiments, each of molecules of the plurality of protected molecules independently has the structure:

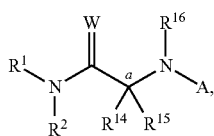

or a salt thereof, wherein W is S or O;

$R^1$ is alkyl, alkenyl, alkynyl, aryl, heteroalkyl, heteroalkenyl, or heteroaryl; and wherein $R^1$ further comprises a solid support;

$R^2$ is hydrogen or alkyl;

$R^{14}$ and $R^{15}$ are the same or different and are independently hydrogen, halo, alkyl, alkenyl, aryl, heteroalkyl, arylalkyl, hydroxyarylalkyl, heteroarylalkyl, cycloalkyl, thioalkyl, selenoalkyl, hydroxyalkyl, or amino-substituted alkyl;

$R^{16}$ is H or alkyl;

A is a functional group comprising a chromophore; and wherein (a) is a carbon center, wherein the carbon center is in an R-configuration, an S-configuration, or is a non-stereogenic center.

In some embodiments, deprotecting of the subset of the plurality of protected molecules comprises contacting the subset of protected molecules with a reagent to form the plurality of deprotected molecules such that the plurality of deprotected molecules produces a lower fluorescent signal compared to the subset of protected molecules. In some embodiments, each of molecules of the plurality of protected molecules independently has the structure:

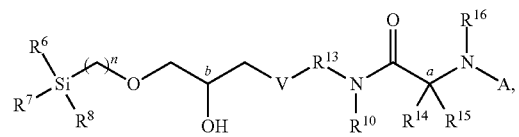

or a salt thereof, wherein V is NH, O, S, or Se;

n=1-6;

$R^6$, $R^7$, and $R^8$ are the same or different and are independently hydrogen, alkyl, alkoxy, silyl, or siloxy, wherein at least one of $R^6$, $R^7$, and $R^8$ further comprises a solid phase;

$R^{10}$ and $R^{16}$ are independently hydrogen or alkyl;

$R^{13}$ is alkyl, heteroalkyl, amino-substituted alkyl, amino-substituted heteroalkyl, amidoalkyl, amidoheteroalkyl, amino-substituted amidoheteroalkyl, each optionally substituted with at least one of alkyl, heteroalkyl, amino-substituted alkyl, amino-substituted heteroalkyl, amidoalkyl, amidoheteroalkyl, or amino-substituted amidoheteroalkyl;

$R^{14}$ and $R^{15}$ are the same or different and are independently hydrogen, halo, alkyl, alkenyl, aryl, heteroalkyl, arylalkyl, hydroxyarylalkyl, heteroarylalkyl, cycloalkyl, thioalkyl, selenoalkyl, hydroxyalkyl, or amino-substituted alkyl;

A is a functional group comprising a chromophore; and (a) is a first carbon center, wherein the first carbon center is in the R-configuration or the S-configuration, or is a non-stereogenic center;

(b) is a second carbon center, wherein the second carbon center is in the R-configuration, the S-configuration.

In some embodiments, the chromophore is a fluorescent chromophore or a phosphorescent chromophore. In some embodiments, $R^{13}$ is ethylenediamino, (ethylenedioxy)bis (ethylamino), tris (2-aminoethyl)amino, polyamidoamino, or polyallylamino. In some embodiments, $R^{14}$ and $R^{15}$ are hydrogen. In some embodiments, the reagent comprises an acid. In some embodiments, the chromophore is degraded. In some embodiments, the reagent comprises ultraviolet light. In some embodiments, the chromophore is photobleached. In some embodiments, methods described herein further comprise forming a first array region, comprising: forming an oxygen-silicon covalent bond between a solid substrate and a first molecule or salt thereof comprising: a silicon at a first end and an epoxide at a second end; forming a V-carbon covalent bond between a carbon atom of said epoxide and a second molecule or salt thereof comprising an amino group, thereby opening the epoxide; wherein V is nitrogen, oxygen, sulfur, or selenium; wherein said epoxide and said silicon are linked by a group comprising an alkyl, alkylether, or alkylthioether, wherein each of alkyl, alkylether, or alkylthioether is optionally substituted with hydroxyl, thiol, amino, or halo. In some embodiments, the first molecule or salt thereof is 3-glycidoxypropyltrimethoxysilane (GPTMS) or a salt thereof.

In some embodiments, the second molecule or salt thereof is ethylenediamine (EDA), (ethylenedioxy)bis(ethylamine) (EDBA), tris (2-aminoethyl)amine (TAEA), polyamidoamine (PAMAM), or polyallylamine (PAAm), or a salt of any of the above. In some embodiments, the second molecule or salt thereof is PAAm or a salt thereof. In some embodiments, the PAAm or salt thereof has a weight average molecular weight of from about 1 KDa to about 100 KDa. In some embodiments, the methods described herein further comprise coupling the amino group to a protected amino acid or salt thereof. In some embodiments, the protected amino acid or salt thereof is a tert-butyl carbamate (Boc)- or 9 fluorenylmethyl carbamate (Fmoc)-protected amino acid or salt thereof.

In some embodiments, the amino acid is glycine or a salt thereof. In some embodiments, the amino acid is serine or a salt thereof. In some embodiments, methods described herein further comprise deprotecting the protected amino acid or salt thereof. In some embodiments, methods described herein further comprise coupling the amino acid or salt thereof to: a protected biotin or salt thereof; or a protected serine or salt thereof; or a chromophoric dye, to form the plurality of protected molecules. In some embodiments, the chromophoric dye is a fluorescent dye or a phosphorescent dye. In some embodiments, detecting alignment further comprises a fluorescence scan. In some embodiments, determining alignment comprises determining alignment of a center of the first array region and a center of the second array region, wherein substantial alignment of the center of the first array region with the center of the second array region indicates proper alignment of a photolithographic mask. In some embodiments, determining alignment comprises determining the uniformity of distance from a boundary of the first array region to a boundary of the second array region, wherein a substantially uniform distance from the boundary of the first array region to the boundary of second array region indicates proper alignment of a photolithographic mask.

Described herein are molecules or salts thereof having the structure:

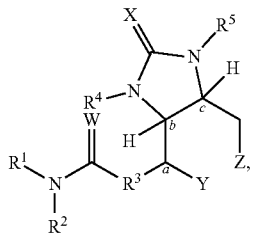

or a salt thereof,
wherein W is S or O;
X is S, O, or NH;
Y and Z are H, or wherein Y and Z are combined to form a S, O, or methylene;
$R^1$ is alkyl, alkenyl, alkynyl, aryl, heteroalkyl, heteroalkenyl, or heteroaryl; and wherein $R^1$ further comprises a solid support;
$R^2$ is hydrogen or alkyl;
$R^3$ is alkyl, alkenyl, aryl, heteroalkyl, heteroalkenyl, heteroaryl, or arylalkyl;
$R^4$ and $R^5$ are independently hydrogen or alkyl, alkenyl, aryl, heteroalkyl, heteroalkenyl, heteroaryl, or arylalkyl; wherein at least one of $R^4$ and $R^5$ is not hydrogen; and (a) is a first carbon center, wherein the first carbon center is in an R-configuration, an S-configuration, or is a non-stereogenic center;
(b) is a second carbon center, wherein the second carbon center is in the R-configuration or the S-configuration; and
(c) is a third carbon center, wherein the third carbon center is in the R-configuration or the S-configuration.

In some embodiments, molecules described herein have the structure:

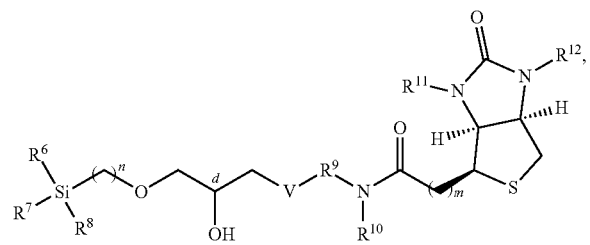

or a salt thereof,
wherein V is NH, O, S, or Se;
n=1-6, m=1-6;
$R^6$, $R^7$, and $R^8$ are the same or different and are independently hydrogen, alkyl, alkoxy, silyl, or siloxy, wherein at least one of $R^6$, $R^7$, and $R^8$ further comprises a solid phase;
$R^9$ is alkyl, alkenyl, alkynyl or aryl, all optionally substituted with at least one of halo, alkyl, polyhaloalkyl, alkyoxy, haloalkoxy, polyhaloalkoxy, alkoxycarbonyl, alkenyl, alkynyl, cycloalkyl, cycloalkylalkyl, hydroxyl, hydroxyalkyl, nitro, cyano, amino, substituted amino, alkylamino, dialkylamino, thiol, alkylthio, alkylcarbonyl, acyl, alkoxycarbonyl, aminocarbonyl, alkylsulfinyl, sulfonamide, or sulfonyl;
$R^{10}$ is hydrogen or alkyl;
$R^{11}$ and $R^{12}$ are independently hydrogen or arylalkyl; wherein at least one of $R^{11}$ and $R^{12}$ is not hydrogen; and
(d) is a carbon center, wherein the carbon center is in the R-configuration or the S-configuration.

In some embodiments, molecules described herein have the structure:

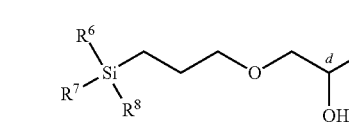
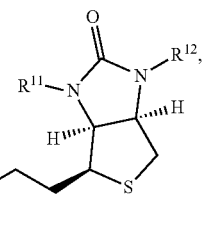

or a salt thereof, wherein V is NH, O, S, or Se;

$R^6$, $R^7$, and $R^8$ are the same or different and are independently hydrogen, alkyl, alkoxy, silyl, or siloxy, wherein at least one of $R^6$, $R^7$, and $R^8$ further comprises a solid phase;

$R^{13}$ is alkyl, heteroalkyl, amino-substituted alkyl, amino-substituted heteroalkyl, amidoalkyl, amidoheteroalkyl, amino-substituted amidoheteroalkyl, each optionally substituted with at least one of alkyl, heteroalkyl, amino-substituted alkyl, amino-substituted heteroalkyl, amidoalkyl, amidoheteroalkyl, or amino-substituted amidoheteroalkyl;

$R^{14}$ and $R^{15}$ are the same or different and are independently hydrogen, halo, alkyl, alkenyl, aryl, heteroalkyl, arylalkyl, hydroxyarylalkyl, heteroarylalkyl, cycloalkyl, thioalkyl, selenoalkyl, hydroxyalkyl, or amino-substituted alkyl;

$R^{11}$ and $R^{12}$ are independently hydrogen or arylalkyl, wherein at least one of $R^4$ and $R^5$ is not hydrogen;

(d) is a first carbon center, wherein the first carbon center is in the R-configuration or the S-configuration; and (e) is a second carbon center, wherein the second carbon center is in the R-configuration, the S-configuration, or is a non-stereogenic center.

In some embodiments, $R^{11}$ is hydrogen and $R^{12}$ is dimethoxytrityl. In some embodiments, $R^{13}$ is ethylenediamino, (ethylenedioxy)bis(ethylamino), tris(2-aminoethyl)amino, polyamidoamino, or polyallylamino. In some embodiments, $R^{14}$ and $R^{15}$ are hydrogen. In some embodiments, $R^{14}$ is hydrogen and $R^{15}$ is hydroxymethyl.

Described herein are molecules or salts thereof having the structure:

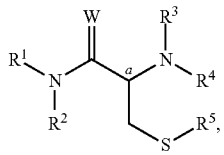

or a salt thereof,
wherein W is S or O;

$R^1$ is alkyl, alkenyl, alkynyl, aryl, heteroalkyl, heteroalkenyl, or heteroaryl; and wherein $R^1$ further comprises a solid support;

$R^2$, $R^3$, and $R^4$ are independently hydrogen or alkyl;

$R^5$ is alkyl, alkenyl, aryl, heteroalkyl, heteroalkenyl, heteroaryl, or arylalkyl; and wherein (a) is a carbon center, wherein the carbon center is in an R-configuration or an S-configuration.

In some embodiments, molecules described herein have the structure:

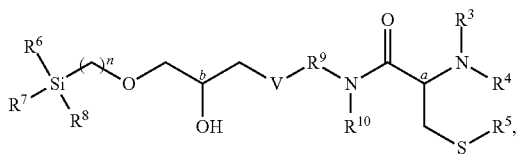

or a salt thereof,
wherein V is NH, O, S, or Se;
n=1-6;

$R^3$ and $R^4$ are independently hydrogen or alkyl;

$R^5$ is alkyl, alkenyl, aryl, heteroalkyl, heteroalkenyl, heteroaryl, or arylalkyl;

$R^6$, $R^7$, and $R^8$ are the same or different and are independently hydrogen, alkyl, alkoxy, silyl, or siloxy, wherein at least one of $R^6$, $R^7$, and $R^8$ further comprises a solid phase;

$R^9$ is alkyl, alkenyl, alkynyl or aryl, all optionally substituted with at least one of halo, alkyl, polyhaloalkyl, alkyoxy, haloalkoxy, polyhaloalkoxy, alkoxycarbonyl, alkenyl, alkynyl, cycloalkyl, cycloalkylalkyl, hydroxyl, hydroxyalkyl, nitro, cyano, amino, substituted amino, alkylamino, dialkylamino, thiol, alkylthio, alkylcarbonyl, acyl, alkoxycarbonyl, aminocarbonyl, alkylsulfinyl, sulfonamide, or sulfonyl;

$R^{10}$ is hydrogen or alkyl; and (a) is a first carbon center, wherein the first carbon center is in the R-configuration or the S-configuration; and (b) is a second carbon center, wherein the second carbon center is in the R-configuration or the S-configuration.

In some embodiments, molecules described herein have the structure:

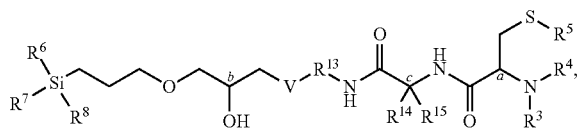

or a salt thereof,
wherein V is NH, O, S, or Se;

$R^3$ and $R^4$ are independently hydrogen or alkyl;

$R^5$ is hydrogen or arylalkyl;

$R^6$, $R^7$, and $R^8$ are the same or different and are independently hydrogen, alkyl, alkoxy, silyl, or siloxy, wherein at least one of $R^6$, $R^7$, and $R^8$ further comprises a solid phase;

$R^{13}$ is alkyl, heteroalkyl, amino-substituted alkyl, amino-substituted heteroalkyl, amidoalkyl, amidoheteroalkyl, amino-substituted amidoheteroalkyl, each optionally substituted with at least one of alkyl, heteroalkyl, amino-substituted alkyl, amino-substituted heteroalkyl, amidoalkyl, amidoheteroalkyl, or amino-substituted amidoheteroalkyl;

$R^{14}$ and $R^{15}$ are the same or different and are independently hydrogen, halo, alkyl, alkenyl, aryl, heteroalkyl, arylalkyl, hydroxyarylalkyl, heteroarylalkyl, cycloalkyl, thioalkyl, selenoalkyl, hydroxyalkyl, or amino-substituted alkyl;

(a) is a carbon center, wherein the carbon center is in the R-configuration or the S-configuration;

(b) is a second carbon center, wherein the second carbon center is in the R-configuration or the S-configuration, or wherein the protected molecules or salts thereof comprise a mixture of the R-configuration and the S-configuration; and (c) is a third carbon center, wherein the third carbon center is in an R-configuration, an S-configuration, or is a non-stereogenic center.

Described herein are molecules or salts thereof having the structure:

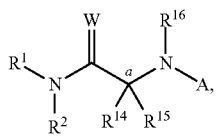

or a salt thereof,
wherein W is S or O;
R$^1$ is alkyl, alkenyl, alkynyl, aryl, heteroalkyl, heteroalkenyl, or heteroaryl; and wherein R$^1$ further comprises a solid support;
R$^2$ hydrogen or alkyl;
R$^{14}$ and R$^{15}$ are the same or different and are independently hydrogen, halo, alkyl, alkenyl, aryl, heteroalkyl, arylalkyl, hydroxyarylalkyl, heteroarylalkyl, cycloalkyl, thioalkyl, selenoalkyl, hydroxyalkyl, or amino-substituted alkyl;
R$^{16}$ is H or alkyl;
A is a functional group comprising a chromophore; and
wherein (a) is a carbon center, wherein the carbon center is in an R-configuration, an S-configuration, or is a non-stereogenic center.

In some embodiments, the chromophore is a fluorescent chromophore or a phosphorescent chromophore. In some embodiments, molecules described herein have the structure:

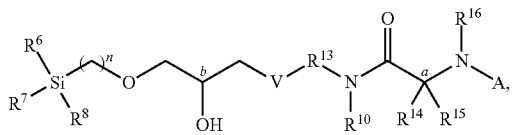

or a salt thereof,
wherein V is NH, O, S, or Se;
n=1-6, m=1-6;
R$^6$, R$^7$, and R$^8$ are the same or different and are independently hydrogen, alkyl, alkoxy, silyl, or siloxy, wherein at least one of R$^6$, R$^7$, and R$^8$ further comprises a solid phase;
R$^{10}$ and R$^{16}$ are independently hydrogen or alkyl;
R$^{13}$ is alkyl, heteroalkyl, amino-substituted alkyl, amino-substituted heteroalkyl, amidoalkyl, amidoheteroalkyl, amino-substituted amidoheteroalkyl, each optionally substituted with at least one of alkyl, heteroalkyl, amino-substituted alkyl, amino-substituted heteroalkyl, amidoalkyl, amidoheteroalkyl, or amino-substituted amidoheteroalkyl;
R$^{14}$ and R$^{15}$ are the same or different and are independently hydrogen, halo, alkyl, alkenyl, aryl, heteroalkyl, arylalkyl, hydroxyarylalkyl, heteroarylalkyl, cycloalkyl, thioalkyl, selenoalkyl, hydroxyalkyl, or amino-substituted alkyl;
(a) is a carbon center, wherein the carbon center is in the R-configuration or the S-configuration, or is a non-stereogenic center; and
(b) is a second carbon center, wherein the second carbon center is in the R-configuration or the S-configuration.

Described herein are arrays comprising a plurality of the molecules, or salts thereof, described herein. Further described herein are arrays comprising at least two peptide features. Further described herein are arrays wherein at least two of the plurality of molecules or salts thereof are cross-linked. Further described herein are arrays comprising instructions for use.

Described herein are methods of making an array, comprising associating molecules or salts described herein with a substrate.

Described herein are methods of making an array, comprising the methods described herein.

Described herein are kits comprising molecules or salts described herein and instructions for use.

Described herein are methods of making a kit, comprising forming the kit with molecules or salts described herein.

Described herein are molecules or salts thereof made by the processes described herein.

Other Embodiments

The section headings used herein are for organizational purposes only and are not to be construed as limiting the subject matter described.

It is to be understood that the methods and compositions described herein are not limited to the particular methodology, protocols, constructs, and reagents described herein and as such may vary. It is also to be understood that the terminology used herein is for the purpose of describing particular embodiments only, and is not intended to limit the scope of the methods and compositions described herein, which will be limited only by the appended claims. While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

Several aspects are described with reference to example applications for illustration. Unless otherwise indicated, any embodiment can be combined with any other embodiment. It should be understood that numerous specific details, relationships, and methods are set forth to provide a full understanding of the features described herein. A skilled artisan, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

Some inventive embodiments herein contemplate numerical ranges. When ranges are present, the ranges include the range endpoints. Additionally, every sub range and value within the rage is present as if explicitly written out. The term "about" or "approximately" can mean within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, within 5-fold, or within 2-fold, of a value. Where particular values are described in the application and claims, unless otherwise stated the term "about" meaning within an acceptable error range for the particular value can be assumed

EXAMPLES

Figure 4:
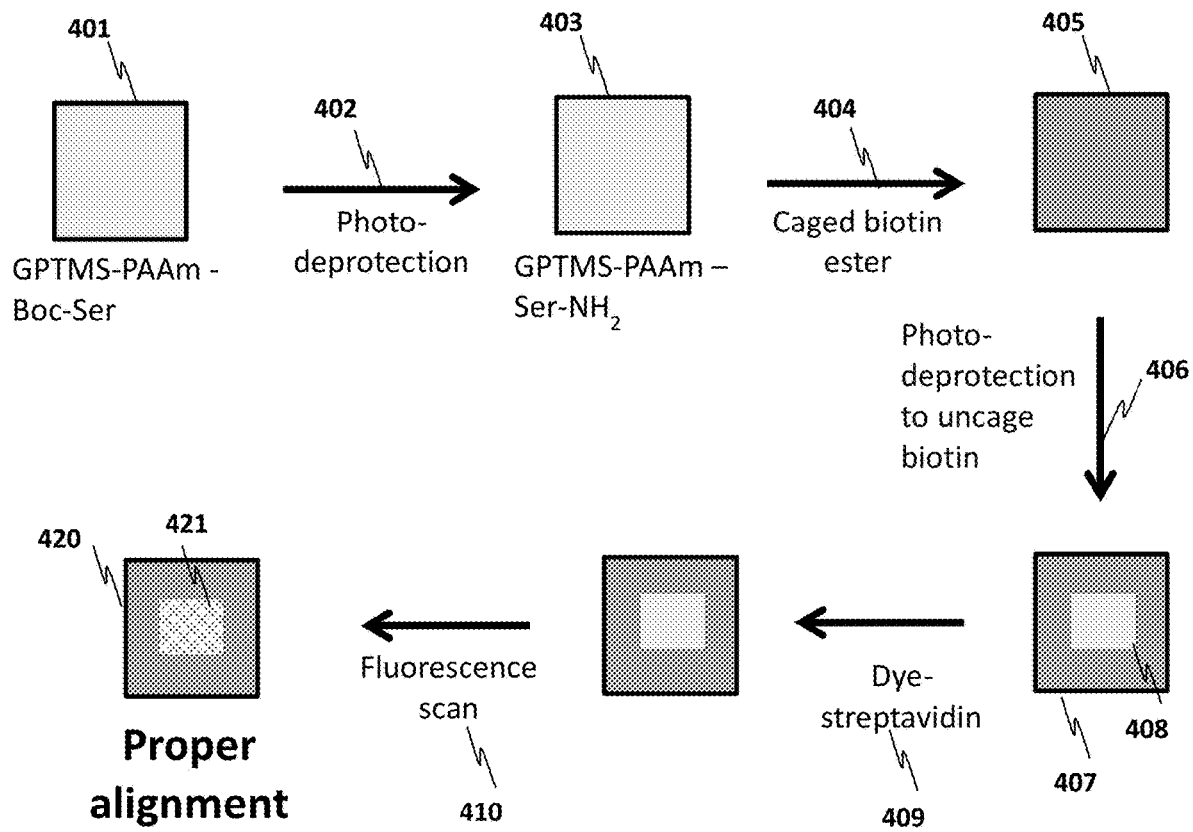
FIG. 4 illustrates an exemplary proper mask alignment.

Example 1. Formation of a Dye-Linked Streptavidin Box-in-Frame with Proper Mask Alignment Referring to FIG. 4, a GPTMS-PAAm-SerBoc base layer 401 is synthesized onto a silicon wafer by sequential deposition of GPTMS, PAAm, and Boc-protected serine. A frame region 403 is formed by photodeprotection 402 of the Boc-protected serine to expose a primary amine, using a photolithographic mask to define the boundary of the frame region subjected to Boc-deprotection. A caged biotin ester 404 is coupled to the primary amines in the frame region of 404 to generate a frame region comprising caged biotin esters 405. Photodeprotection 406 is applied to uncage a portion of the biotin and produce a box region 408 in the frame region 407, using a photolithographic mask to define the boundary of box region subjected to photodeprotection. Dye-linked-streptavidin 409 is applied to the wafer, associating the dye specifically to the uncaged biotin in the box region via a tight biotin-streptavidin interaction. A fluorescence scan 410 is then applied. Bright fluorescence of the streptavidin-linked dye in box region 421 is visualized against a comparatively weaker fluorescence of the caged biotin in the surrounding frame region 420. The relative positions of the box region 421 and the frame region 420 are used to determine the quality of photolithographic mask alignment. FIG. 4 illustrates proper mask alignment, wherein the box region 421 and the frame region 420 are co-centered.

Figure 5:
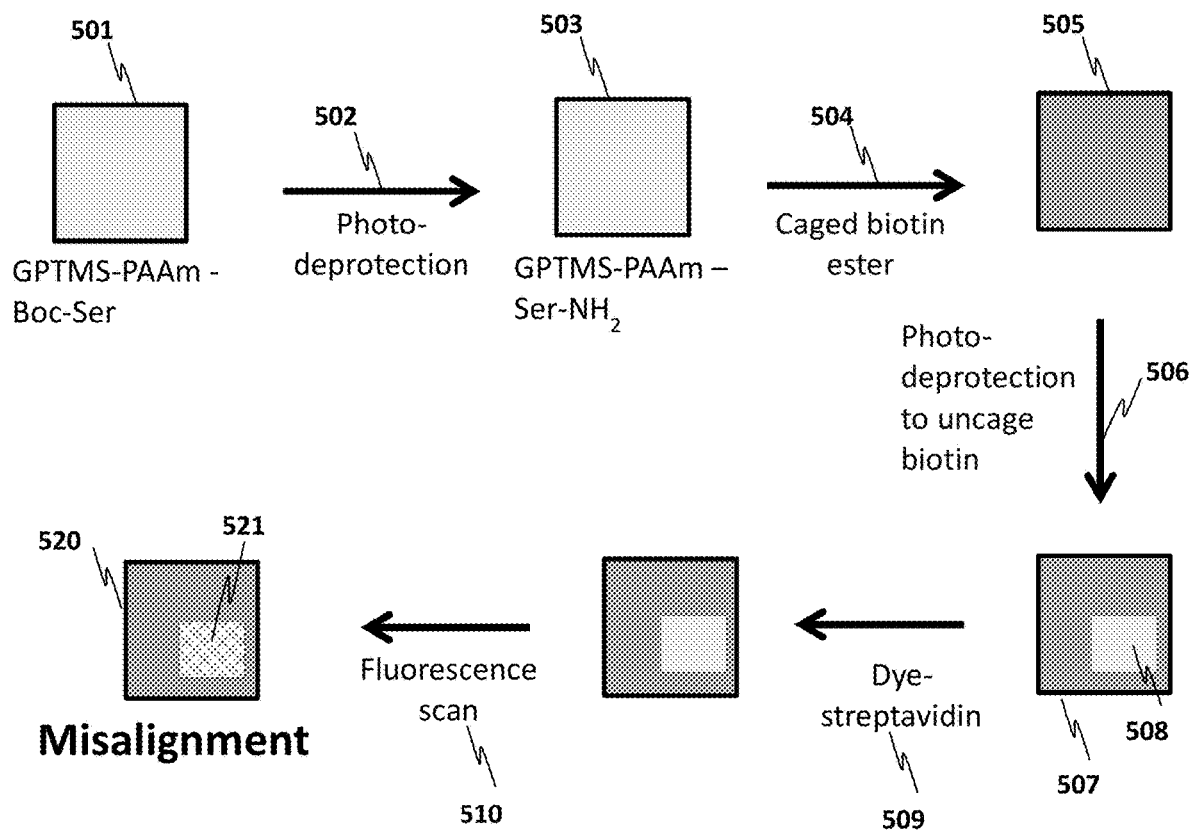
FIG. 5 illustrates an exemplary mask misalignment.

Example 2. Formation of a Streptavidin-Linked Dye Box-in-Frame with Improper Mask Alignment Referring to FIG. 5, a GPTMS-PAAm-SerBoc base layer 501 is synthesized onto a silicon wafer by sequential deposition of GPTMS, PAAm, and Box-protected serine. A frame region 503 is formed by photodeprotection 502 of the Boc-protected serine to expose a primary amine, using a photolithographic mask to define the boundary of the frame region subjected to Boc-deprotection. A caged biotin ester 504 is coupled to the primary amines in the frame region to generate a frame region comprising caged biotin esters 505. Photodeprotection 506 is applied to uncage a portion of the biotin and produce a box region 506 in the frame region 507, using a photolithographic mask to define the boundary of box region subjected to photodeprotection. Dye-linked-streptavidin 509 is applied to the wafer, associating the dye specifically to the uncaged biotin in the box region via a tight biotin-streptavidin interaction. A fluorescence scan 510 is then applied. Bright fluorescence of the streptavidin-linked dye in box region 521 is visualized against a comparatively weaker fluorescence of the caged biotin in the surrounding frame region 520. The relative positions of the box region 521 and the frame region 520 are used to determine the quality of photolithographic mask alignment. FIG. 5 illustrates improper mask alignment, wherein the box region 521 and the frame region 520 are not co-centered.

Example 3. Formation of a Streptavidin-Linked Dye Box-in-Frame

Figure 6:
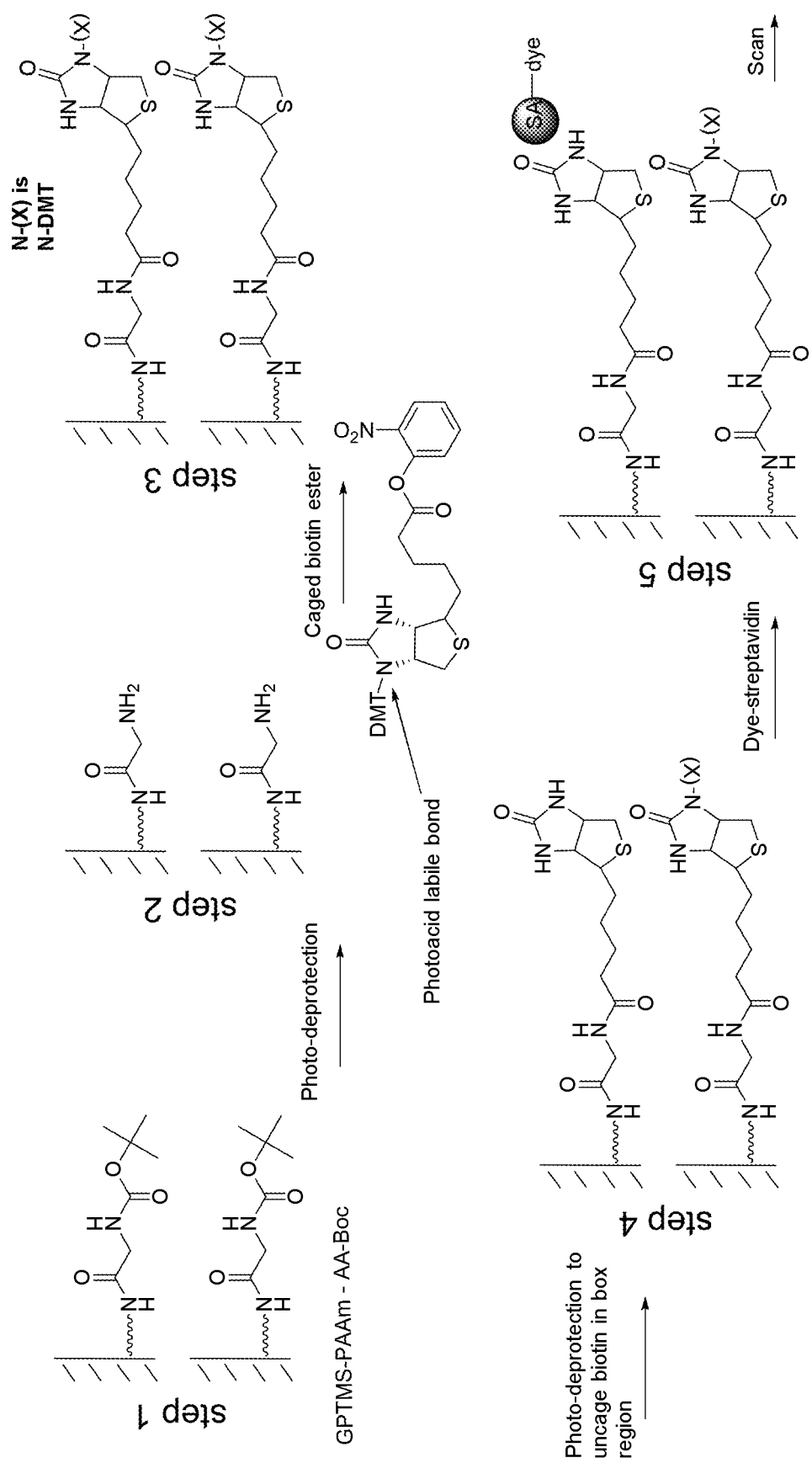
FIG. 6 illustrates a chemical process of alignment.

Referring to FIG. 6, in step 1, a GPTMS-PAAm-GlyBoc base layer is synthesized onto a silicon wafer by sequential deposition of GPTMS, PAAm, and Boc-protected glycine. In step 2, a frame region is formed by photodeprotection of the Boc-protected glycine to expose a primary amine, using a photolithographic mask to define the boundary of the frame region. In step 3, a dimethoxytrityl (DMT)-caged biotin orthonitrophenylester is coupled to the free amine within the frame region. In step 4, photodeprotection is applied to uncage a portion of the DMT-caged biotin to produce a box region within the frame region, using a photolithographic mask to define the boundary of the box region subjected to deprotection. In step 5, dye-linked streptavidin is applied to the wafer, associating the dye specifically to the uncaged biotin in the box region via a tight biotin-streptavidin interaction. A fluorescence scan is then applied. Bright fluorescence of the streptavidin-linked dye in the box region is visualized against a comparatively weaker fluorescence of the caged biotin in the surrounding frame region, and the relative positions of the box region and the frame region are used to determine the quality of photolithographic mask alignment, wherein co-centering of the box region and the frame region is indicative of proper mask alignment.

Example 4. Formation of a Cysteine-Linked Dye Box-in-Frame

Figure 7:
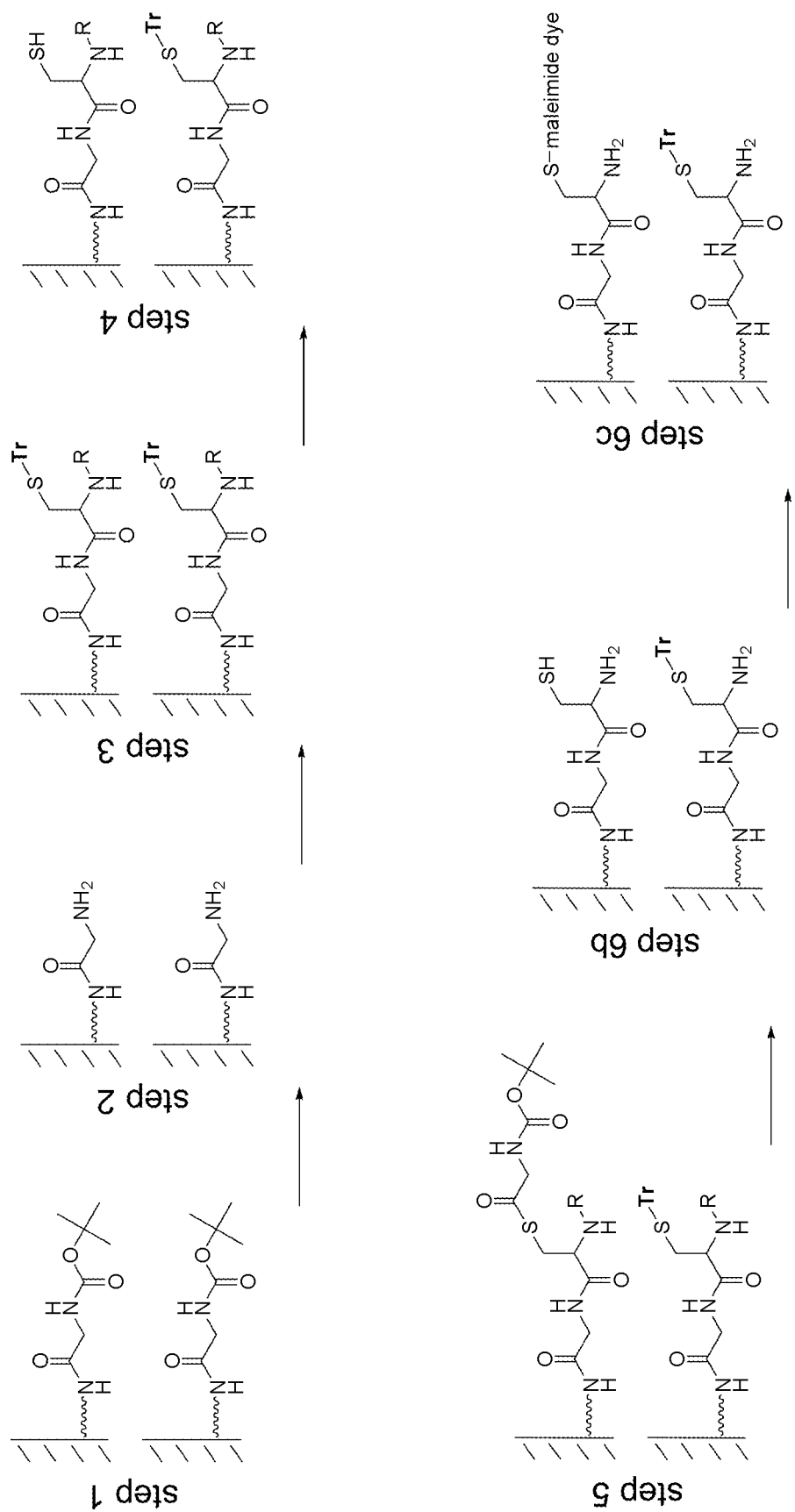
FIG. 7 illustrates a chemical process of alignment.

Referring to FIG. 7, in step 1, a GPTMS-PAAm-GlyBoc base layer is synthesized onto a silicon wafer by sequential deposition of GPTMS, PAAm, and Boc-protected glycine. In step 2, a frame region is formed by photodeprotection of the Boc-protected glycine to expose a primary amine, using a photolithographic mask to define the boundary of the frame region. In step 3, a Cys-trityl amino acid monomer is coupled to the free amine within the frame region. In step 4, photodeprotection using a photoacid or photoacid generator is applied to deprotect a portion of the Cys-trityl protecting group to form a free sulfhydryl group, thereby forming a box region within the frame region, using a photolithographic mask to define the boundary of the box region subjected to deprotection. In step 5, synthesis of peptide features on the array is completed using solid phase peptide coupling, resulting in at least partial functionalization of the free sulfhydryl group in the box region, and the slides are diced from the wafer. In step 6b, the slide is treated with ammonia or sodium hydroxide to remove any peptide coupling products from the cysteine, reexposing the sulfhydryl group. In step 6c, the sulfhydryl is coupled to a maleimide dye. A fluorescence scan is then applied. Bright fluorescence of the sulfhydryl-linked dye in the box region is visualized against a comparatively weaker fluorescence of the Cys-trityl groups in the surrounding frame region. The relative positions of the box region and the frame region are used to determine the quality of photolithographic mask alignment, wherein co-centering of the box region and the frame region is indicative of proper mask alignment.

Example 5. Formation of a Degraded Dye Box-in-Frame

Figure 8:
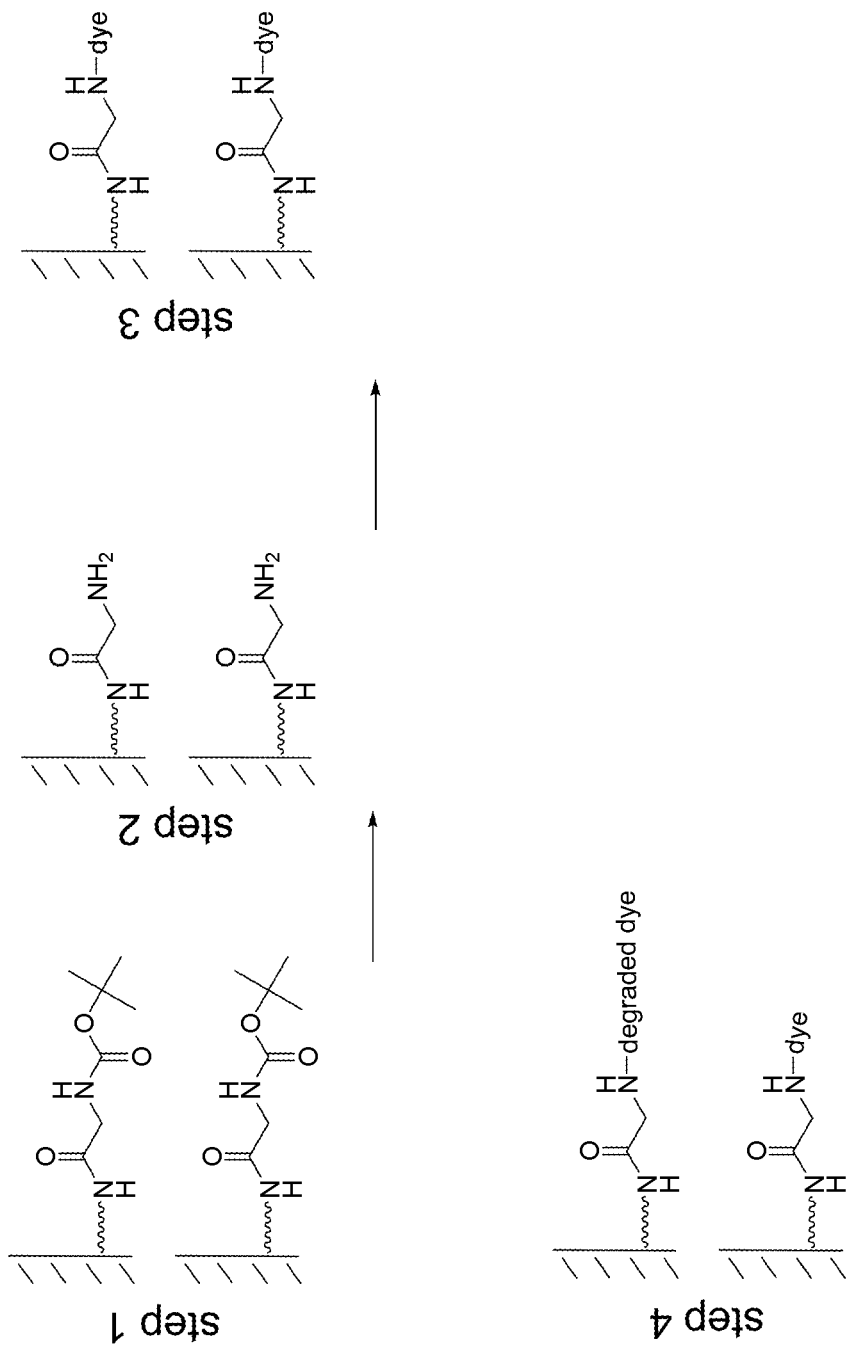
FIG. 8 illustrates a chemical process of alignment.

Referring to FIG. 8, in step 1, a GPTMS-PAAm-GlyBoc base layer is synthesized onto a silicon wafer by sequential deposition of GPTMS, PAAm, and Boc-protected glycine.

In step 2, a frame region is formed by photodeprotection of the Boc-protected glycine to expose a primary amine, using a photolithographic mask to define the boundary of the frame region. In step 3, a UV or acid-sensitive dye is coupled to the primary amine within the frame region. For UV sensitive dyes, in step 4, UV light is applied to photobleach a portion of the UV-sensitive dye to form a degraded dye, thereby forming a box region within the frame region, using a photolithographic mask to define the boundary of the box region subjected to deprotection. For acid-sensitive dyes, in step 4, photodegradation using a photoacid or photoacid generator is applied to degrade a portion of the acid-sensitive dye to form a degraded dye, thereby forming a box region within the frame region, using a photolithographic mask to define the boundary of the box region subjected to deprotection. A fluorescence scan is then applied. Relative lack of fluorescence of the degraded dye in the box region is visualized against a comparatively stronger fluorescence of the undegraded dye in the surrounding frame region. The relative positions of the box region and the frame region are used to determine the quality of photolithographic mask alignment, wherein co-centering of the box region and the frame region is indicative of proper mask alignment.

Example 6. Peptide Synthesis with a Streptavidin-Linked Dye Box-in-Frame

Figure 9:
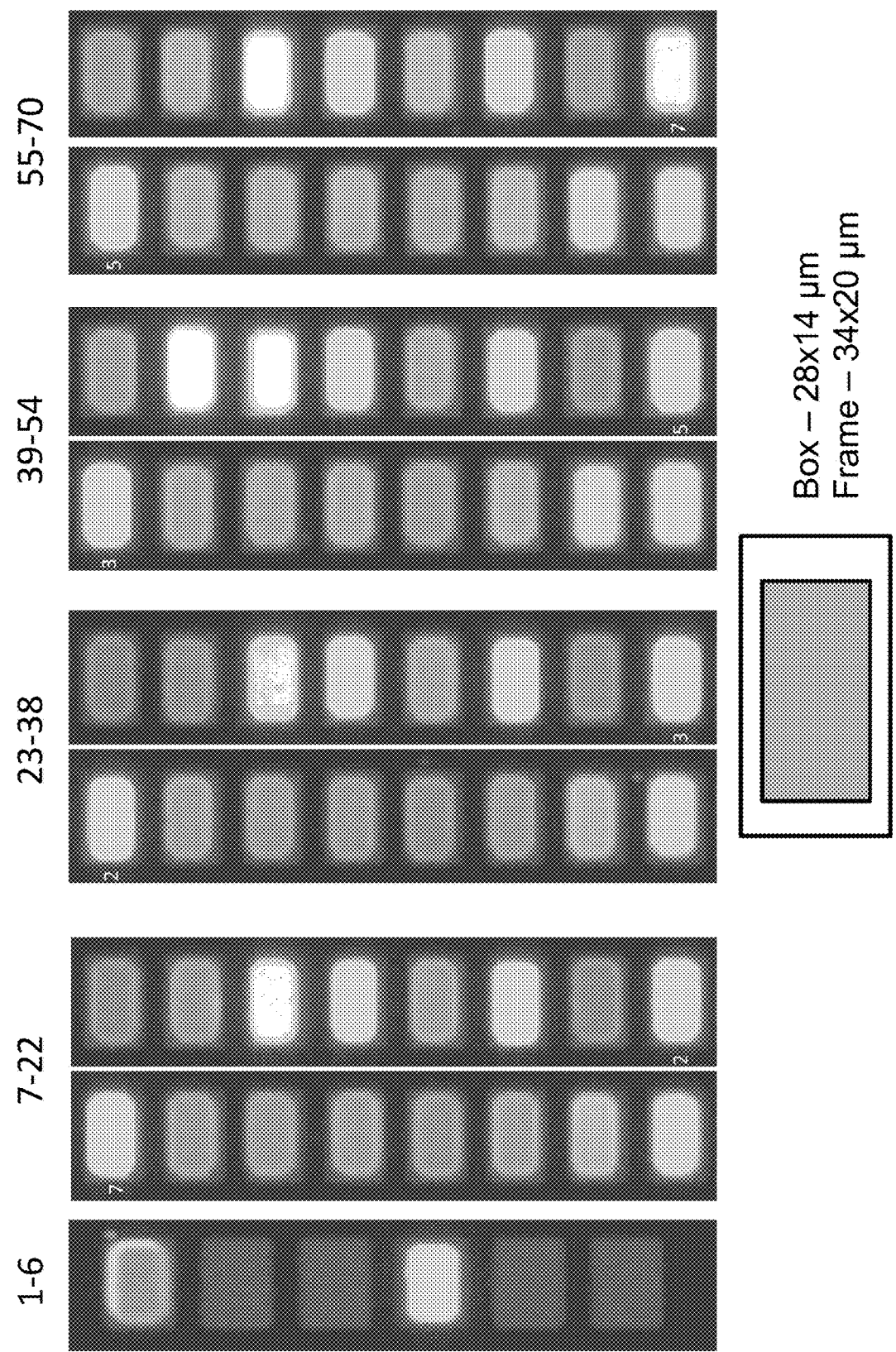
FIG. 9 illustrates a fluorescence imaging of alignment controlling spots.

An array of 64-mer polypeptides was synthesized using standard peptide coupling reagents and steps, with modification. After each synthesis step, an alignment determination was conducted using the general protocol of Example 1. Fluorescence measurements were obtained and recorded for each determination, as shown in FIG. 9. Fluorescence measured at spots and 1 and 4 confirmed that masks were successfully aligned "in-frame". Various misalignment conditions were then detected, for example, qualitatively: spot 25 is "high", spot 53 is "low", spot 40 is "left", spot 37 is "right". Qualitatively, spot 38 is properly aligned relative to other spots measured.

What is claimed is:
1. A method comprising:
   a. deprotecting a subset of a plurality of protected molecules comprising a photoreactive or acid-sensitive protecting group to form a plurality of deprotected molecules; wherein the plurality of protected molecules are comprised in a first array region; wherein the plurality of deprotected molecules are comprised in a second array region; and wherein a distance from a boundary of the first array region to a boundary of the second array region is substantially uniform; and
   b. detecting alignment of the second array region with the first array region, wherein the detecting alignment comprises detecting a chromophoric signal from at least one of the first array region and the second array region; and wherein the first array region and the second array region are substantially located in a space between two or more peptide features, wherein the method further comprises forming a first array region, comprising:
      i) forming an oxygen-silicon covalent bond between a solid substrate and a first molecule or salt thereof comprising a silicon at a first end and an epoxide at a second end;
      ii) forming a V-carbon covalent bond between a carbon atom of said epoxide and a second molecule or salt thereof comprising an amino group, thereby opening the epoxide;

wherein V is nitrogen, oxygen, sulfur, or selenium;
wherein said epoxide and said silicon are linked by a group comprising an alkyl, alkylether, or alkylthioether, wherein each of alkyl, alkylether, or alkylthioether is optionally substituted with hydroxyl, thiol, amino, or halo, and wherein the first array region further comprises coupling, wherein an amino acid or salt thereof is further coupled to: a protected biotin or salt thereof; or a protected serine or salt thereof; or a chromophoric dye, to form the plurality of protected molecules.

2. The method of claim 1, wherein the chromophoric signal is a fluorescent signal or a phosphorescent signal.

3. The method of claim 1, wherein the distance from the boundary of the first array region to the boundary of the second array region is non-zero.

4. The method of claim 1, wherein deprotecting a subset of a plurality of protected molecules comprises a photolithographic mask.

5. The method of claim 1, wherein deprotecting the subset of the plurality of protected molecules comprises contacting the subset of protected molecules with a reagent to form the plurality of deprotected molecules such that the plurality of deprotected molecules produces a higher fluorescent signal compared to the subset of the protected molecules.

6. The method of claim 1, wherein the method steps are repeated at least once to synthesize a peptide.

7. The method of claim 1, further comprising determining alignment of a center of the first array region and a center of the second array region, wherein substantial alignment of the center of the first array region with the center of the second array region indicates proper alignment of a photolithographic mask.

8. The method of claim 1, further comprising determining the uniformity of distance from a boundary of the first array region to a boundary of the second array region, wherein a substantially uniform distance from the boundary of the first array region to the boundary of second array region indicates proper alignment of a photolithographic mask.

9. The method of claim 1, wherein at least some of molecules of the plurality of protected molecules independently has the structure (I):

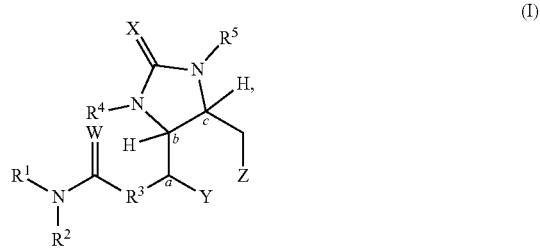

or a salt thereof,
wherein W is S or O;
X is S, O, or NH;
Y and Z are H, or wherein Y and Z are combined to form a S, O, or methylene;
$R^1$ is alkyl, alkenyl, alkynyl, aryl, heteroalkyl, heteroalkenyl, or heteroaryl; and wherein $R^1$ further comprises a solid support;
$R^2$ is hydrogen or alkyl;
$R^3$ is alkyl, alkenyl, aryl, heteroalkyl, heteroalkenyl, heteroaryl, or arylalkyl;

$R^4$ and $R^5$ are independently hydrogen, alkyl, alkenyl, aryl, heteroalkyl, heteroalkenyl, heteroaryl, or arylalkyl; wherein at least one of $R^4$ and $R^5$ is not hydrogen; and (a) is a first carbon center, wherein the first carbon center is in an R-configuration, an S-configuration, or is a non-stereogenic center;

(b) is a second carbon center, wherein the second carbon center is in the R-configuration or the S-configuration; and (c) is a third carbon center, wherein the third carbon center is in the R-configuration or the S-configuration.

10. The method of claim 1, wherein each of molecules of the plurality of protected molecules thereof independently has the structure (IA):

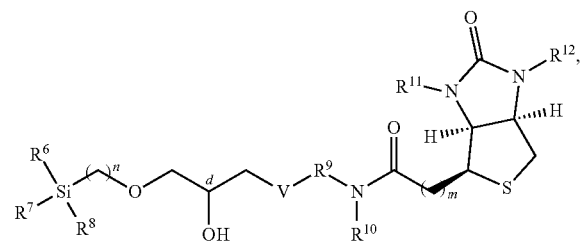

(IA)

or a salt thereof,
wherein V is NH, O, S, or Se;
n=1-6, m=1-6;
$R^6$, $R^7$, and $R^8$ are the same or different and are independently hydrogen, alkyl, alkoxy, silyl, or siloxy, wherein at least one of $R^6$, $R^7$, and $R^8$ further comprises a solid phase;
$R^9$ is alkyl, alkenyl, alkynyl or aryl, all optionally substituted with at least one of halo, alkyl, polyhaloalkyl, alkyoxy, haloalkoxy, polyhaloalkoxy, alkoxycarbonyl, alkenyl, alkynyl, cycloalkyl, cycloalkylalkyl, hydroxyl, hydroxyalkyl, nitro, cyano, amino, substituted amino, alkylamino, dialkylamino, thiol, alkylthio, alkylcarbonyl, acyl, alkoxycarbonyl, aminocarbonyl, alkylsulfinyl, sulfonamide, or sulfonyl;
$R^{10}$ is hydrogen or alkyl;
$R^{11}$ and $R^{12}$ are independently hydrogen or arylalkyl; wherein at least one of $R^{11}$ and $R^{12}$ is not hydrogen; and
(d) is a carbon center, wherein the carbon center is in the R-configuration or the S-configuration.

11. The method of claim 1, wherein at least some of molecules of the plurality of protected molecules independently has the structure (II):

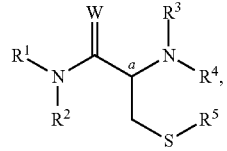

(II)

or a salt thereof,
wherein W is S or O;
$R^1$ is alkyl, alkenyl, alkynyl, aryl, heteroalkyl, heteroalkenyl, or heteroaryl; and wherein $R^1$ further comprises a solid support;

$R^2$, $R^3$, and $R^4$ are independently hydrogen or alkyl;
$R^5$ is hydrogen, alkyl, alkenyl, aryl, heteroalkyl, heteroalkenyl, heteroaryl, or arylalkyl; and
wherein (a) is a carbon center, wherein the carbon center is in an R-configuration or an S-configuration.

12. The method of claim 1, wherein at least some of molecules of the plurality of protected independently has the structure (IIA):

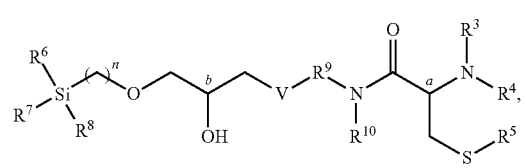

(IIA)

or a salt thereof,
wherein V is NH, O, S, or Se;
n=1-6;
$R^3$ and $R^4$ are independently hydrogen or alkyl;
$R^5$ is alkyl, alkenyl, aryl, heteroalkyl, heteroalkenyl, heteroaryl, or arylalkyl;
$R^6$, $R^7$, and $R^8$ are the same or different and are independently hydrogen, alkyl, alkoxy, silyl, or siloxy, wherein at least one of $R^6$, $R^7$, and $R^8$ further comprises a solid phase;
$R^9$ is alkyl, alkenyl, alkynyl or aryl, all optionally substituted with at least one of halo, alkyl, polyhaloalkyl, alkyoxy, haloalkoxy, polyhaloalkoxy, alkoxycarbonyl, alkenyl, alkynyl, cycloalkyl, cycloalkylalkyl, hydroxyl, hydroxyalkyl, nitro, cyano, amino, substituted amino, alkylamino, dialkylamino, thiol, alkylthio, alkylcarbonyl, acyl, alkoxycarbonyl, aminocarbonyl, alkylsulfinyl, sulfonamide, or sulfonyl;
$R^{10}$ is hydrogen or alkyl; and
(a) is a first carbon center, wherein the first carbon center is in an R-configuration or an S-configuration; and
(b) is a second carbon center, wherein the second carbon center is in the R-configuration or the S-configuration.

13. The method of claim 1, wherein at least some of molecules of the plurality of protected molecules independently has the structure (IIB):

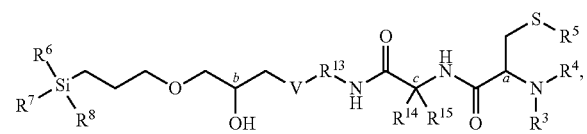

(IIB)

or a salt thereof,
wherein V is NH, O, S, or Se;
$R^3$ and $R^4$ are independently hydrogen or alkyl;
$R^5$ is hydrogen or arylalkyl;
$R^6$, $R^7$, and $R^8$ are the same or different and are independently hydrogen, alkyl, alkoxy, silyl, or siloxy, wherein at least one of $R^6$, $R^7$, and $R^8$ further comprises a solid phase;
$R^{13}$ is alkyl, heteroalkyl, amino-substituted alkyl, amino-substituted heteroalkyl, amidoalkyl, amidoheteroalkyl, amino-substituted amidoheteroalkyl, each optionally substituted with at least one of alkyl, heteroalkyl, amino-substituted alkyl, amino-substituted heteroalkyl, amidoalkyl, amidoheteroalkyl, or amino-substituted amidoheteroalkyl, $R^{14}$ and $R^{15}$ are the same or different and are independently hydrogen, halo, alkyl, alkenyl, aryl, heteroalkyl, arylalkyl, hydroxyarylalkyl, heteroarylalkyl, cycloalkyl, thioalkyl, selenoalkyl, hydroxyalkyl, or amino-substituted alkyl;

(a) is a carbon center, wherein the carbon center is in the R-configuration or the S-configuration;

(b) is a second carbon center, wherein the second carbon center is in the R-configuration or the S-configuration; and (c) is a third carbon center, wherein the third carbon center is in the R-configuration, the S-configuration, or is a non-stereogenic center.

14. The method of claim 1, wherein each of molecules of the plurality of protected molecules independently has the structure (III):

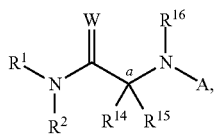

(III)

or a salt thereof,
wherein W is S or O;
$R^1$ is alkyl, alkenyl, alkynyl, aryl, heteroalkyl, heteroalkenyl, or heteroaryl; and wherein $R^1$ further comprises a solid support;
$R^2$ is hydrogen or alkyl;
$R^{14}$ and $R^{15}$ are the same or different and are independently hydrogen, halo, alkyl, alkenyl, aryl, heteroalkyl, arylalkyl, hydroxyarylalkyl, heteroarylalkyl, cycloalkyl, thioalkyl, selenoalkyl, hydroxyalkyl, or amino-substituted alkyl;
$R^{16}$ is H or alkyl;

A is a functional group comprising a chromophore; and
wherein (a) is a carbon center, wherein the carbon center is in an R-configuration, an S-configuration, or is a non-stereogenic center.

15. The method of claim 1, wherein each of molecules of the plurality of protected molecules independently has the structure (IIIA):

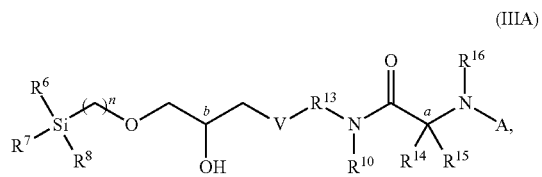

(IIIA)

or a salt thereof,
wherein V is NH, O, S, or Se;
n=1-6;
$R^6$, $R^7$, and $R^8$ are the same or different and are independently hydrogen, alkyl, alkoxy, silyl, or siloxy,
wherein at least one of $R^6$, $R^7$, and $R^8$ further comprises a solid phase;
$R^{10}$ and $R^{16}$ are independently hydrogen or alkyl;
$R^{13}$ is alkyl, heteroalkyl, amino-substituted alkyl, amino-substituted heteroalkyl, amidoalkyl, amidoheteroalkyl, amino-substituted amidoheteroalkyl, each optionally substituted with at least one of alkyl, heteroalkyl, amino-substituted alkyl, amino-substituted heteroalkyl, amidoalkyl, amidoheteroalkyl, or amino-substituted amidoheteroalkyl;
$R^{14}$ and $R^{15}$ are the same or different and are independently hydrogen, halo, alkyl, alkenyl, aryl, heteroalkyl, arylalkyl, hydroxyarylalkyl, heteroarylalkyl, cycloalkyl, thioalkyl, selenoalkyl, hydroxyalkyl, or amino-substituted alkyl;
A is a functional group comprising a chromophore; and
(a) is a first carbon center, wherein the first carbon center is in the R-configuration or the S-configuration, or is a non-stereogenic center;
(b) is a second carbon center, wherein the second carbon center is in the R-configuration, the S-configuration.

* * * * *